US008012986B2

(12) United States Patent
Gatti McArthur et al.

(10) Patent No.: US 8,012,986 B2
(45) Date of Patent: Sep. 6, 2011

(54) PYRIDINE AND PYRIMIDINE DERIVATIVES AS MGLUR2 ANTAGONISTS

(75) Inventors: Silvia Gatti McArthur, Basel (CH); Juergen Wichmann, Steinen (DE); Thomas Woltering, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 657 days.

(21) Appl. No.: 12/053,648

(22) Filed: Mar. 24, 2008

(65) Prior Publication Data

US 2008/0280924 A1 Nov. 13, 2008

(30) Foreign Application Priority Data

Apr. 2, 2007 (EP) ..................... 07105429

(51) Int. Cl.
*C07D 401/04* (2006.01)
*A61K 31/506* (2006.01)
(52) U.S. Cl. ......... 514/256; 514/275; 544/331; 544/333
(58) Field of Classification Search ............ 544/331, 544/333; 514/256, 275
See application file for complete search history.

(56) References Cited

FOREIGN PATENT DOCUMENTS

| WO | WO 02/068417 | 9/2002 |
|---|---|---|
| WO | WO 2004/089308 | 10/2004 |
| WO | WO 2006/082002 | 8/2006 |
| WO | WO 2007/110337 | 10/2007 |

OTHER PUBLICATIONS

D'Onofrio et al., J. Neurochem. (2003) vol. 84(6) pp. 1288-1295.
Klapars et al., J. Am. Chem. Soc. (2002) vol. 124(50) pp. 14844-14845.
Thorand et al., J. Of Organic Chem. (1998) vol. 63(23) pp. 8551-8553.
Lila et al., Synthetic Communications (1998) vol. 28(23) pp. 4419-4429.
Heirtzler, F. et al, *Synlett*, No. 8, (1999) p. 1203-1206, XP002934351.
Crane, J. et al, *Chem Abstracts Svs*, Accession No. 1993:15425 XP002483383.

*Primary Examiner* — Deepak Rao
(74) *Attorney, Agent, or Firm* — George W. Johnston; Patricia S. Rocha-Tramaloni; Kimberly J. Prior

(57) ABSTRACT

The present invention relates to compounds of formula (I)

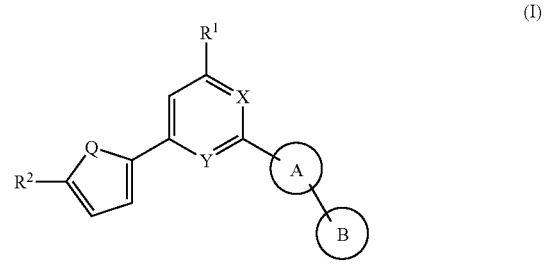

(I)

wherein A, B, Q, X, Y, $R^1$, and $R^2$ are as defined herein; pharmaceutical compositions containing them; a process for their manufacture; and methods for treating CNS disorders with the same.

25 Claims, No Drawings

PYRIDINE AND PYRIMIDINE DERIVATIVES AS MGLUR2 ANTAGONISTS

PRIORITY TO RELATED APPLICATION(S)

This application claims the benefit of European Patent Application No. 07105429.0, filed Apr. 2, 2007, which is hereby incorporated by reference in its entirety.

BACKGROUND OF THE INVENTION

In the central nervous system (CNS) the transmission of stimuli takes place by the interaction of a neurotransmitter, which is sent out by a neuron, with a neuroreceptor.

L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) form the second main group and, furthermore, belong to the family of G-protein-coupled receptors.

At present, eight different members of these mGluR are known and of these some even have sub-types. On the basis of structural parameters, the different influences on the synthesis of secondary metabolites and the different affinity to low-molecular weight chemical compounds, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the group II can be used for the treatment or prevention of acute and/or chronic neurological disorders such as psychosis, schizophrenia, Alzheimer's disease, cognitive disorders and memory deficits. Other treatable indications in this connection are restricted brain function caused by bypass operations or transplants, poor blood supply to the brain, spinal cord injuries, head injuries, hypoxia caused by pregnancy, cardiac arrest and hypoglycemia. Further treatable indications are chronic and acute pain, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia, depressions, colon cancer, sleep disorders, disorders of circadian rhythms and glioma since mGluR2 antagonists have been found to reduce cell proliferation in human glioma cells (J. Neurochem. March 2003, 84(6): 1288-95). Objects of the present invention are compounds of formula (I) and their pharmaceutically acceptable salts per se and as pharmaceutically active substances, their manufacture, medicaments based on a compound in accordance with the invention and their production, as well as the use of the compounds in accordance with the invention in the control or prevention of illnesses of the aforementioned kind, and, respectively, for the production of corresponding medicaments.

SUMMARY OF THE INVENTION

The present invention provides compounds of formula (I), pharmaceutical compositions containing them, a process for their manufacture, and methods of treating CNS disorders.

In particular, the present invention provides compounds of formula (I)

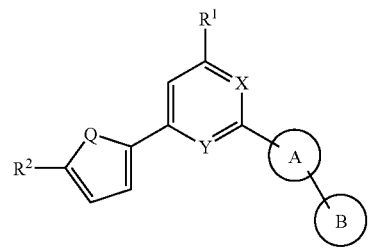

(I)

wherein
either one of X or Y is N and the other is CH, or both X and Y are N;
Q is S, O, —CH═N— or —N═CH—;
A is aryl or 5 or 6 membered heteroaryl each of which is optionally substituted by $C_{1-6}$-alkyl;
B is an optionally substituted aryl or an optionally substituted 5 or 6 membered heteroaryl, wherein the substituents are selected from the group consisting of:
halo,
nitro,
$C_{1-6}$-alkyl optionally substituted by hydroxy,
$NR^{a}R^{b}$, wherein $R^{a}$ and $R^{b}$ are independently H, $C_{1-6}$-alkyl or —(CO)—$C_{1-6}$-alkyl,
—S—$C_{1-6}$-alkyl,
—($SO_2$)—OH,
—($SO_2$)—$C_{1-6}$-alkyl,
—($SO_2$)—$NR^{c}R^{d}$, wherein $R^{c}$ and $R^{d}$ are independently:
H,
$C_{1-6}$-alkyl optionally substituted by hydroxy,
$C_{1-6}$-haloalkyl,
$C_{1-6}$-alkoxy,
—(CO)$C_{1-6}$-alkyl optionally substituted by $C_{1-6}$-alkoxy,
—($CH_2CH_2O$)$_n$$CHR^{e}$, wherein $R^{e}$ is H or $CH_2OH$ and n is 1, 2, 3, 4, 5, 6, 7, 8, 9 or 10,
—($CH_2$)$_m$-aryl, wherein m is 1 or 2 and the aryl is optionally substituted by halo or $C_{1-6}$-alkoxy,
—($CH_2$)$_p$—$C_{3-6}$-cycloalkyl, wherein p is 0 or 1, or
5 or 6-membered heterocycloalkyl,
—($SO_2$)—$NR^{f}R^{g}$, wherein $R^{f}$ and $R^{g}$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of:
hydroxy, $C_{1-6}$-alkyl, $C_{1-6}$-alkoxy which is optionally substituted by hydroxy, and
5 or 6 membered heteroaryloxy,
$NHSO_2$—$C_{1-6}$-alkyl, and
$NHSO_2$—$NR^{h}R^{i}$ wherein $R^{h}$ and $R^{i}$ are each independently H, $C_{1-6}$-alkyl, —(CO)O—$C_{1-6}$-alkyl, or $R^{h}$ and $R^{i}$ together with the nitrogen atom to which they are attached form a 4, 5 or 6 membered heterocycloalkyl ring optionally containing a further heteroatom selected from nitrogen, oxygen and sulphur, wherein said 4, 5 or 6 membered heterocycloalkyl ring is optionally substituted by $C_{1-6}$-alkyl,
$R^1$ is H, halogen, $C_{1-6}$-alkyl optionally substituted by hydroxy, $C_{1-6}$-alkoxy, $C_{1-6}$-haloalkyl, or $C_{3-6}$-cycloalkyl;

$R^2$ is selected from the group consisting of cyano, halogen, $C_{1-6}$-haloalkyl, $C_{1-6}$-alkoxy, $C_{1-6}$-haloalkoxy, $C_{1-6}$-alkyl and $C_{3-6}$-cycloalkyl;

or is $NR^jR^k$ wherein $R^j$ and $R^k$ are each independently selected from the group consisting of H, $C_{3-8}$-cycloalkyl, aryl, heteroaryl having from 5 to 12 ring atoms and $C_{1-6}$-alkyl each of which is optionally substituted by one or more substituent(s) selected from the group consisting of halogen, hydroxy, $C_{3-8}$-cycloalkyl, aryl, heteroaryl having from 5 to 12 ring atoms and —$NR^lR^m$, wherein $R^l$ and $R^m$ are independently selected from the group consisting of H and $C_{1-6}$-alkyl;

or $R^l$ and $R^m$ can, together with the nitrogen atom to which they are attached, form an optionally substituted heterocyclic group having 5 to 12 ring atoms optionally containing a further heteroatom selected from nitrogen, oxygen and sulphur, wherein said heterocyclic group is optionally substituted by one, two, three, four or five substituents which are selected from the group consisting of halogen, hydroxy, $C_{1-6}$-alkyl and $C_{1-6}$-haloalkyl;

as well as pharmaceutically acceptable salts thereof.

The compounds of formula (I) can also be used in form of their prodrugs. Examples are esters, N-oxides, phosphate esters, glycoamide esters, glyceride conjugates and the like. The prodrugs can add to the value of the present compounds advantages in absorption, pharmacokinetics in distribution and transport to the brain.

Compounds of formula I are metabotropic glutamate receptor antagonists. Compounds of formula I are distinguished by valuable therapeutic properties.

DETAILED DESCRIPTION OF THE INVENTION

Unless otherwise stated, the following terms used in the present description have the definitions given in the following.

The term "alkyl" denotes straight-chain or branched saturated hydrocarbon residue with 1 to 6 carbon atoms ($C_{1-6}$-alkyl), preferably with 1 to 4 carbon atoms, such as methyl, ethyl, n-propyl, i-propyl, i-butyl, t-butyl, as well as those groups which are illustrated with the exemplified compounds of the invention hereinafter.

The term "$C_{1-6}$-haloalkyl" denotes a $C_{1-6}$-alkyl group as defined hereinabove, which is substituted by one or more halogen atom(s), in particular Cl, F or I, preferably three Cl or two or three F, i.e. $CCl_3$, $CHF_2$ and $CF_3$ as well as those groups which are specifically illustrated with the exemplified compounds of the invention hereinafter.

The term "$C_{1-6}$-alkoxy" denotes a $C_{1-6}$-alkyl residue as defined hereinabove bound via an oxygen atom. Examples of "$C_{1-6}$-alkoxy" residues include methoxy, ethoxy, isopropoxy, as well as those groups which are illustrated with the exemplified compounds of the invention hereinafter.

The term "$C_{1-6}$-haloalkoxy" denotes a $C_{1-6}$-alkoxy group as defined hereinabove, which is substituted by one or more halogen atom(s), in particular Cl, F or I, preferably three Cl or two or three F, i.e. $OCHF_2$ and $OCF_3$, $OCH_2CHF_2$, $OCH_2CF_3$ as well as those groups which are specifically illustrated with the exemplified compounds of the invention hereinafter.

The term "aryl" denotes a monovalent cyclic aromatic hydrocarbon radical, for example phenyl, naphthyl, biphenyl or indanyl.

The term "heteroaryl or 5 or 6-membered heteroaryl or heteroaryl having from 5 to 12 ring atoms" refers to an aromatic ring system having 5 to 6 or 5 to 12 ring atoms and containing one or more, in particular, one, two, three, four or five and preferably one, two or three heteroatoms selected from nitrogen, oxygen and sulphur. Examples of such heteroaryl groups include thiophenyl, imidazolyl, oxadiazolyl, pyrrolyl, pyrazolyl, pyridinyl, pyrazinyl, pyrimidinyl or pyridazinyl, and in particular, [1,2,4]oxadiazolyl, pyridin-2-yl, pyridin-3-yl, pyridine-4-yl, pyrimidin-5-yl, thiazol-2-yl and thiophen-2-yl as well as those groups which are illustrated with the exemplified compounds of the invention hereinafter.

The term "heteroaryloxy" denotes a heteroaryl group, including 5 or 6-membered heteroaryl or heteroaryl having from 5 to 12 ring atoms as defined hereinabove, which is connected via an oxygen atom.

The term "halogen" embraces fluorine (F), chlorine (Cl), bromine (Br) and iodine (I).

The terms "$C_{3-6}$-cycloalkyl or $C_{5-8}$-cycloalkyl" mean a nonaromatic carbocyclic group containing 3 to 6 or 5 to 8 carbon atoms, such as cyclopropyl, cyclobutyl, cyclopentyl or cyclohexyl as those groups which are illustrated with the exemplified compounds of the invention hereinafter.

The term "5 or 6-membered or 5 to 12-membered heterocycloalkyl" denotes a nonaromatic heterocyclic ring having 5 or 6 or 5 to 12 ring members comprising at least two carbon atoms as ring member and 1, 2 or 3 additional heteroatom(s) ring members selected from N, O and S, the remaining ring members being carbon atoms. Examples of 5 or 12 heterocycloalkyl rings include but are not limited to 1H-tetrazole; 2H-tetrazole; 1,2,3- and 1,2,4-triazole; imidazole; pyrrole; 1,2,3-, 1,3,4- or 1,2,5-thiadiazine; 1,4-oxazine; 1,2- or 1,4-thiazine; 4-morpholinyl; 1-pyrrolidinyl; 1-piperazinyl, preferably 4-morpholinyl; 1-pyrrolidinyl or 1-piperazinyl as well as those groups which are illustrated with the exemplified compounds of the invention hereinafter. Substituents for such 5 or 6 membered heterocyclic ring include but are not limited to halo, amino, nitro, cyano, hydroxy, $C_{1-6}$-alkyl optionally substituted by hydroxy, $C_{1-6}$-alkoxy, $C_{1-6}$-alkenyl, $C_{3-8}$-cycloalkyl, or $CF_3$, and preferably $C_{1-6}$-alkyl or $CF_3$ as well as those groups which are illustrated with the exemplified compounds of the invention hereinafter.

The term "optionally substituted" means that the chemical group to which it refers can be substituted by one or more of the substituents recited in this connection, for example by one, two, three, four, five, six, seven, eight, nine or ten substituents, depending on the valence and available positions of said chemical group.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable addition salt" refers to any salt derived from an inorganic or organic acid or base.

"Therapeutically effective amount" means an amount that is effective to prevent, alleviate or ameliorate symptoms of disease or prolong the survival of the subject being treated.

The compounds of formula (I) and their pharmaceutically acceptable salts are metabotropic glutamate receptor antagonists and can be used for the treatment or prevention of acute and/or chronic neurological disorders, such as psychosis, schizophrenia, Alzheimer's disease, cognitive disorders and memory deficits. Other treatable indications are restricted brain function caused by bypass operations or transplants, poor blood supply to the brain, spinal cord injuries, head injuries, hypoxia caused by pregnancy, cardiac arrest and hypoglycemia. Further treatable indications are acute and chronic pain, Huntington's chorea, ALS, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, nicotine addiction, psychoses, opiate addiction, anxiety, vomiting, dyskinesia, depression, colon cancer, sleep disorders, disorders of circadian rhythms and glioma.

Also encompassed by the compounds of formula (I) according to the invention are the compounds wherein:
both X and Y are N or X is N and Y is CH;
Q is S, —CH═N—, or —N═CH—;
A is aryl or 5 or 6 membered heteroaryl;
B is an optionally substituted aryl or an optionally substituted 5 or 6 membered heteroaryl,
wherein the substituents are selected from the group consisting of
$NR^aR^b$, wherein $R^a$ and $R^b$ are independently H,
—($SO_2$)—$NR^cR^d$, wherein $R^c$ and $R^d$ are independently:
H,
$C_{1-6}$-alkyl, and
—(CO)$C_{1-6}$-alkyl;
$R^1$ is $C_{1-6}$-alkyl or $C_{1-6}$-haloalkyl; and
$R^2$ is 5 or 6 membered heteroaryl optionally substituted by one, two or three substituents selected from the group consisting of $C_{1-6}$-haloalkyl;
as well as pharmaceutically acceptable salts thereof.

Also encompassed by the compounds of formula (I) according to the invention are the compounds of formula (Ia):

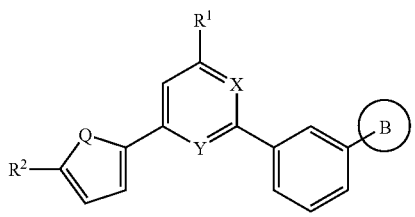

(Ia)

wherein X, Y, Q, B, $R^1$ and $R^2$ are as described hereinabove for formula (I).

In a certain embodiment of the compounds of formula (Ia), B is an optionally substituted aryl or an optionally substituted 5 or 6 membered heteroaryl, wherein the substituent is $NR^aR^b$, wherein $R^a$ and $R^b$ are both H, for example the following compounds:
5-{3-[4-(5-Chloro-thiophen-2-yl)-6-trifluoromethyl-pyrimidin-2-yl]-phenyl}-pyridin-2-ylamine;
5-{3-[4-(5-Chloro-thiophen-2-yl)-6-trifluoromethyl-pyrimidin-2-yl]-phenyl}-pyrimidin-2-ylamine;
5-{3-[4-Trifluoromethyl-6-(6-trifluoromethyl-pyridin-3-yl)-pyrimidin-2-yl]-phenyl}-pyridin-2-ylamine; and
5-[3-(6'-Methyl-6-trifluoromethyl-[3,4']bipyridinyl-2'-yl)-phenyl]-pyridin-2-ylamine.

In a certain embodiment of the compounds of formula (Ia), B is an optionally substituted aryl or an optionally substituted 5 or 6 membered heteroaryl, wherein the substituent is $NR^aR^b$, wherein $R^a$ and $R^b$ are H and —($SO_2$)—$NR^cR^d$, wherein $R^c$ and $R^d$ are independently H, $C_{1-6}$-alkyl, or —(CO)$C_{1-6}$-alkyl, for example the following compounds:
3'-[4-Trifluoromethyl-6-(6-trifluoromethyl-pyridin-3-yl)-pyrimidin-2-yl]-biphenyl-3-sulfonic acid amide;
5-{3-[4-Trifluoromethyl-6-(6-trifluoromethyl-pyridin-3-yl)-pyrimidin-2-yl]-phenyl}-thiophene-2-sulfonic acid amide;
3'-[4-(5-Chloro-thiophen-2-yl)-6-trifluoromethyl-pyrimidin-2-yl]-biphenyl-3-sulfonic acid amide;
5-{3-[4-(5-Chloro-thiophen-2-yl)-6-trifluoromethyl-pyrimidin-2-yl]-phenyl}-thiophene-2-sulfonic acid amide;
3'-[4-Difluoromethyl-6-(6-trifluoromethyl-pyridin-3-yl)-pyrimidin-2-yl]-biphenyl-3-sulfonic acid amide;
5-{3-[4-Difluoromethyl-6-(6-trifluoromethyl-pyridin-3-yl)-pyrimidin-2-yl]-phenyl}-thiophene-2-sulfonic acid amide;
3'-[4-Methyl-6-(6-trifluoromethyl-pyridin-3-yl)-pyrimidin-2-yl]-biphenyl-3-sulfonic acid amide;
5-{3-[4-Methyl-6-(6-trifluoromethyl-pyridin-3-yl)-pyrimidin-2-yl]-phenyl}-thiophene-2-sulfonic acid amide;
3'-(6'-Methyl-6-trifluoromethyl-[3,4']bipyridinyl-2'-yl)-biphenyl-3-sulfonic acid tert-butylamide;
5-[3-(6'-Methyl-6-trifluoromethyl-[3,4']bipyridinyl-2'-yl)-phenyl]-pyridin-2-ylamine;
3'-(6'-Methyl-6-trifluoromethyl-[3,4']bipyridinyl-2'-yl)-biphenyl-3-sulfonic acid amide; and
5-[3-(6'-Methyl-6-trifluoromethyl-[3,4']bipyridinyl-2'-yl)-phenyl]-thiophene-2-sulfonic acid amide.

Also encompassed by the compounds of formula (I) according to the invention are the compounds of formula (Ib):

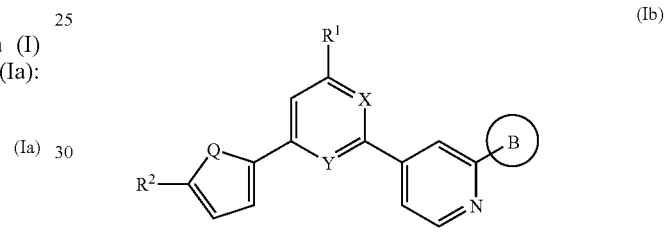

(Ib)

wherein X, Y, Q, B, $R^1$ and $R^2$ are as described hereinabove for formula (I).

In a certain embodiment of the compounds of formula (Ib), B is an optionally substituted aryl or an optionally substituted 5 or 6 membered heteroaryl, wherein the substituent is $NR^aR^b$, wherein $R^a$ and $R^b$ are both H, for example the following compound: 4-[4-Trifluoromethyl-6-(6-trifluoromethyl-pyridin-3-yl)-pyrimidin-2-yl]-[2,3']bipyridinyl-6'-ylamine.

In a certain embodiment of the compounds of formula (Ib), B is an optionally substituted aryl or an optionally substituted 5 or 6 membered heteroaryl, wherein the substituent is $NR^aR^b$, wherein $R^a$ and $R^b$ are H and —($SO_2$)—$NR^cR^d$, wherein $R^c$ and $R^d$ are independently H, $C_{1-6}$-alkyl, or —(CO)$C_{1-6}$-alkyl, for example the following compounds:
3-{4-[4-Trifluoromethyl-6-(6-trifluoromethyl-pyridin-3-yl)-pyrimidin-2-yl]-pyridin-2-yl}-benzenesulfonamide;
5-{4-[4-Trifluoromethyl-6-(6-trifluoromethyl-pyridin-3-yl)-pyrimidin-2-yl]-pyridin-2-yl}-thiophene-2-sulfonic acid amide;
N-Propionyl-3-{4-[4-trifluoromethyl-6-(6-trifluoromethyl-pyridin-3-yl)-pyrimidin-2-yl]-pyridin-2-yl}-benzenesulfonamide;
3-{4-[4-Difluoromethyl-6-(6-trifluoromethyl-pyridin-3-yl)-pyrimidin-2-yl]-pyridin-2-yl}-benzenesulfonamide;
5-{4-[4-Difluoromethyl-6-(6-trifluoromethyl-pyridin-3-yl)-pyrimidin-2-yl]-pyridin-2-yl}-thiophene-2-sulfonic acid amide;
3-{4-[4-Methyl-6-(6-trifluoromethyl-pyridin-3-yl)-pyrimidin-2-yl]-pyridin-2-yl}-benzenesulfonamide; and
5-{4-[4-Methyl-6-(6-trifluoromethyl-pyridin-3-yl)-pyrimidin-2-yl]-pyridin-2-yl}-thiophene-2-sulfonic acid amide.

Also encompassed by the compounds of formula (I) according to the invention are the compounds of formula (Ic):

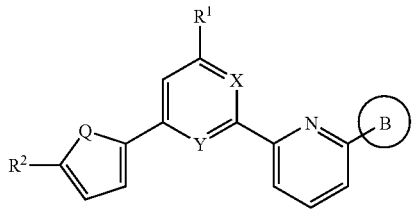

(Ic)

wherein X, Y, Q, B, $R^1$ and $R^2$ are as described hereinabove for formula (I).

In a certain embodiment of the compounds of formula (Ic), B is an optionally substituted aryl or an optionally substituted 5 or 6 membered heteroaryl, wherein the substituent is $NR^aR^b$, wherein $R^a$ and $R^b$ are H and —$(SO_2)$—$NR^cR^d$, wherein $R^c$ and $R^d$ are independently H, $C_{1-6}$-alkyl, or —$(CO)C_{1-6}$-alkyl, for example the following compounds:

N-tert-Butyl-3-{6-[4-methyl-6-(6-trifluoromethyl-pyridin-3-yl)-pyrimidin-2-yl]-pyridin-2-yl}-benzenesulfonamide;
N-tert-Butyl-3-{6-[4-methyl-6-(6-trifluoromethyl-pyridin-3-yl)-pyrimidin-2-yl]-pyridin-2-yl}-benzenesulfonamide;
3-{6-[4-Methyl-6-(5-trifluoromethyl-pyridin-2-yl)-pyrimidin-2-yl]-pyridin-2-yl}-benzenesulfonamide;
3-{6-[4-Methyl-6-(6-trifluoromethyl-pyridin-3-yl)-pyrimidin-2-yl]-pyridin-2-yl}-benzenesulfonamide;
N-tert-Butyl-3-(6'-methyl-6"-trifluoromethyl-[2,2';4',3"]terpyridin-6-yl)-benzenesulfonamide; and
3-(6'-Methyl-6"-trifluoromethyl-[2,2';4',3"]terpyridin-6-yl)-benzenesulfonamide.

Also encompassed by the compounds of formula (I) according to the invention are the compounds of formula (Id):

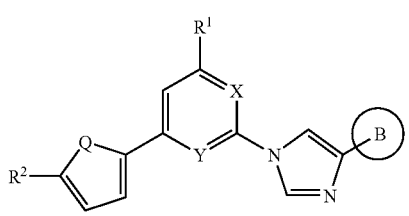

(Id)

wherein X, Y, Q, B, $R^1$ and $R^2$ are as described hereinabove for formula (I).

In a certain embodiment of the compounds of formula (Id), B is an optionally substituted aryl or an optionally substituted 5 or 6 membered heteroaryl, wherein the substituent is $NR^aR^b$, wherein $R^a$ and $R^b$ are both H, for example the following compounds:

5-{1-[4-Trifluoromethyl-6-(6-trifluoromethyl-pyridin-3-yl)-pyrimidin-2-yl]-1H-imidazol-4-yl}-pyridin-2-ylamine;
5-{1-[4-Difluoromethyl-6-(6-trifluoromethyl-pyridin-3-yl)-pyrimidin-2-yl]-1H-imidazol-4-yl}-pyridin-2-ylamine; and
5-{1-[4-Methyl-6-(6-trifluoromethyl-pyridin-3-yl)-pyrimidin-2-yl]-1H-imidazol-4-yl}-pyridin-2-ylamine.

In a certain embodiment of the compounds of formula (Id), B is an optionally substituted aryl or an optionally substituted 5 or 6 membered heteroaryl, wherein the substituent is $NR^aR^b$, wherein $R^a$ and $R^b$ are H and —$(SO_2)$—$NR^cR^d$, wherein $R^c$ and $R^d$ are independently H, $C_{1-6}$-alkyl, or —$(CO)C_{1-6}$-alkyl, for example the following compounds:

3-{1-[4-(5-Chloro-thiophen-2-yl)-6-trifluoromethyl-pyrimidin-2-yl]-1H-imidazol-4-yl}-benzenesulfonamide; and
5-{1-[4-Methyl-6-(6-trifluoromethyl-pyridin-3-yl)-pyrimidin-2-yl]-1H-imidazol-4-yl}-pyridin-2-ylamine.

The invention also encompasses processes for the preparation of the compounds of the invention.

The compounds of the invention can be prepared by a process comprising the steps of reacting a compound of formula (X):

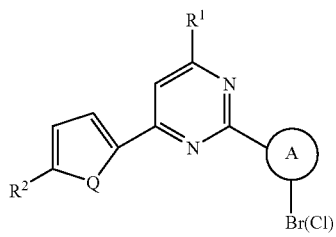

(X)

with a boronic acid derivative of group B, wherein B is a defined hereinabove and a catalyst, to obtain the compound formula (XV):

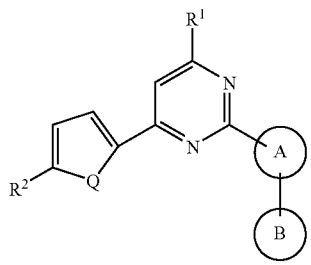

(XV)

wherein A, B, Q, $R^1$ and $R^2$ are as defined hereinabove.

The catalyst can be tetrakis(triphenylphosphine)-palladium.

The reaction can be performed in an organic solvent, e.g. dioxane.

The starting products, intermediates products and reagents for this process are either commercially available or can be prepared as described in the examples hereinafter.

The compounds of the invention can also be prepared by a process comprising the steps of reacting a compound of formula (XXVI):

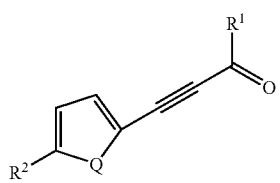

(XXVI)

with a compound of formula (XXX):

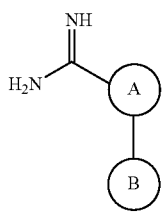

(XXX)

wherein A, B, Q, R¹ and R² are as defined hereinabove.

The starting products, intermediates products and reagents for this process are either commercially available or can be prepared as described in the examples hereinafter.

All detailed procedures for the respective compounds can be found in the description of the examples.

The present invention also provides pharmaceutical compositions containing compounds of the invention, for example compounds of formula I and their pharmaceutically suitable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts and, if desired, one or more other therapeutically valuable substances into a galenical administration form together with one or more therapeutically inert carriers.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The present invention relates also to the methods of treating acute and/or chronic which comprises administering to an individual a therapeutically effective amount of a compound of formula (I) or a pharmaceutically acceptable salts thereof.

The compounds of the present invention are group II mGlu receptor antagonists. The compounds show activities, as measured in the assay described below, of 0.250 µM or less, typically 0.100 µM or less, and ideally of 0.010 µM or less. In the table below are described some specific Ki values of some representative compounds.

| Ex. No. | 1 | 2 | 3 | 4 | 5 | 8 | 9 |
|---|---|---|---|---|---|---|---|
| K₁ mGlu2 (µM) | 0.0116 | 0.0018 | 0.012 | 0.0143 | 0.139 | 0.0156 | 0.0053 |
| Ex. No. | 10 | 12 | 13 | 17 | 19 | 20 | 25 |
| K₁ mGlu2 (µM) | 0.0066 | 0.0033 | 0.033 | 0.0035 | 0.015 | 0.062 | 0.105 |

| Ex. No. | 29 | 30 | 33 |
|---|---|---|---|
| K₁ mGlu2 (µM) | 0.026 | 0.002 | 0.042 |

[³H]-LY354740 Binding on mGlu2 Transfected CHO Cell Membranes.

Transfection and Cell Culture cDNA encoding the rat mGlu2 receptor protein in pBluescript II was subcloned into the eukaryotic expression vector pcDNA I-amp from Invitrogen Ltd (Paisley, UK). This vector construct (pcD1mGR²) was co-transfected with a psvNeo plasmid encoding the gene for neomycin resistance, into CHO cells by a modified calcium phosphate method described by Chen & Okayama (1988). The cells were maintained in Dulbecco's Modified Eagle medium with reduced L-glutamine (1 mM final concentration), 36 mg/L L-Proline and 10% dialysed foetal calf serum from Gibco-Invitrogen; the medium was supplemented with 500 microM α-methyl-4-carboxyphenylglycine (MCPG). Selection was made in the presence of G-418 (300 ug/ml final concentration). Clones were identified by reverse transcription of 5 µg total RNA, followed by PCR using mGlu2 receptor specific primers 5'-atcactgcttgggtttctggcactg-3' and 5'-agcatcactgtgggtggcataggagc-3' in 60 mM Tris HCl (pH 10), 15 mM (NH₄)₂SO₄, 2 mM MgCl₂, 25 units/ml Taq Polymerase with 30 cycles annealing at 60° C. for 1 min., extension at 72° C. for 30 s, and 1 min. 95° C. denaturation.

Membrane Preparation

Cells, cultured as above, were harvested and washed three times with cold PBS and frozen at −80° C. The pellet was resuspended in cold 20 mM HEPES-NaOH buffer containing 10 mM EDTA (pH 7.4), and homogenised with a polytron (Kinematica, AG, Littau, Switzerland) for 10 s at 10 000 rpm. After centrifugation for 30 min. at 4° C., the pellet was washed once with cold 20 mM HEPES-NaOH buffer containing 0.1 mM EDTA, (pH 7.4). After a second centrifugation for 30 min. at 4° C. the pellet was resuspended in cold 20 mM HEPES-NaOH buffer containing 0.1 mM EDTA, (pH 7.4). Protein content was measured using the Micro BCA method from Pierce-Perbio (Rockford, Ill., USA) using bovine serum albumin as standard.

[$^3$H]-LY354740 Binding

After thawing, the membranes were resuspended in cold 50 mM Tris-HCl buffer containing 2 mM $MgCl_2$ (pH 7.4) (binding buffer). The final concentration of the membranes in the assays was 25 μg protein/ml. Inhibition experiments were performed with membranes incubated with 10 nM [$^3$H]-LY354740 at room temperature, for 1 hour, in presence of various concentrations of the compound to be tested. Following the incubations, membranes were filtered onto Whatmann GF/B glass fiber filters or onto GF/B Unifilter plates and washed 5 times with cold binding buffer. Non specific binding was measured in the presence of 10 μM (2S,2'R,3'R)-2-(2'3'-Dicarboxycyclopropyl)glycine (DCG IV from Tocris, Ellisville, Mo. USA). After transfer of the filters into plastic vials containing 10 ml of Ultima-gold scintillation fluid from Perkin-Elmer (Boston, Mass., USA), the radioactivity was measured by liquid scintillation in a Tri-Carb 2500 TR counter (Packard, Zürich, Switzerland). For 96-Unifilter plates the radioactivity was measured after addition of Microscint 40 scintillation fluid (Perkin Elmer, Boston Mass.) using a Top-Count NXT (Packard)

Data Analysis.

The inhibition curves were fitted with a four parameter logistic equation giving $IC_{50}$ values, and Hill coefficients.

Synthesis of 2-chloro- and 2-iodo-pyrimidines

In the following schemes and unless otherwise specified, A, B, Q, $R^1$ and $R^2$ are as defined hereinabove.

General Procedure I

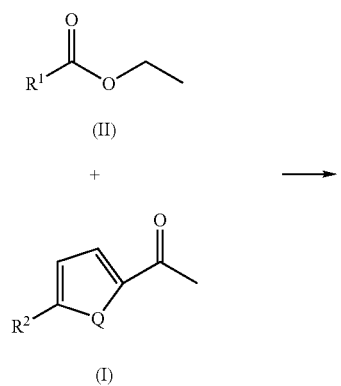

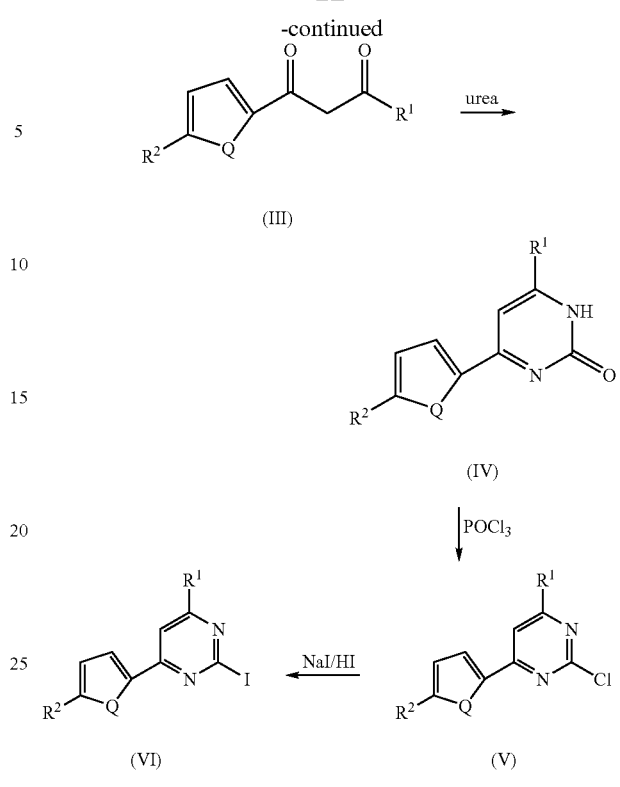

Step 1: To a stirred solution of compound of formula (I) in an organic solvent (e.g. tert-butyl-methyl-ether) is added at room temperature a solution of sodium methanolate in methanol followed by a solution of a compound of formula (II) in an organic solvent (e.g. tert-butyl-methyl-ether). The reaction mixture is stirred at room temperature for about 19 h, cooled, acidified and extracted (e.g. with diethyl ether). The combined organic layers are washed and dried (e.g. $MgSO_4$) and evaporated to give crude the compound of formula (III) which can be used without further purification.

Step 2: To a stirred solution of a compound of formulae III (1 eq) and urea (2 eq) in an organic solvent (e.g. MeOH) is added conc. HCl (e.g. MeOH/HCl 10:1). The reaction mixture is heated under reflux conditions for about 40 h, water is added and the mixture is stirred at 0° C. for 1 h. The precipitate is collected by filtration, washed with water and recrystallized (e.g. diethyl ether/hexan) to yield the compound of formulae IV.

Step 3: To a stirred solution of a compound of formulae IV in phosphoroxychloride is added DMF (5-10 drops) and the reaction mixture is stirred at 115° C. for around 16 h, evaporated and ice-water is added. The water layer is extracted twice (e.g. with diethyl ether), the combined organic layer washed (water followed by brine), dried (e.g. $MgSO_4$) and evaporated to yield the compound of formulae V.

Step 4: To a stirred solution of a compound of formulae V (1 eq) in an organic solvent (e.g. 2-butanone) is added sodium iodide (3.5 eq) and hydroiodic acid (57% in water, 1 eq). The reaction mixture is heated under reflux conditions for around 16 h, cooled and poured into ice/sat. sodium bicarbonate solution. The water layer is extracted twice (e.g. with diethyl ether), the combined organic layer washed (water followed by brine), dried (e.g. $MgSO_4$) and evaporated. Further purification by column chromatography on silica gel (e.g toluene) yields the compound of formulae VI.

Synthesis of 2-bromo-, 2-iodo- and
2-trifluoromethanesulfonyloxy-4-aryl-pyridines
General procedures Ia and Ib

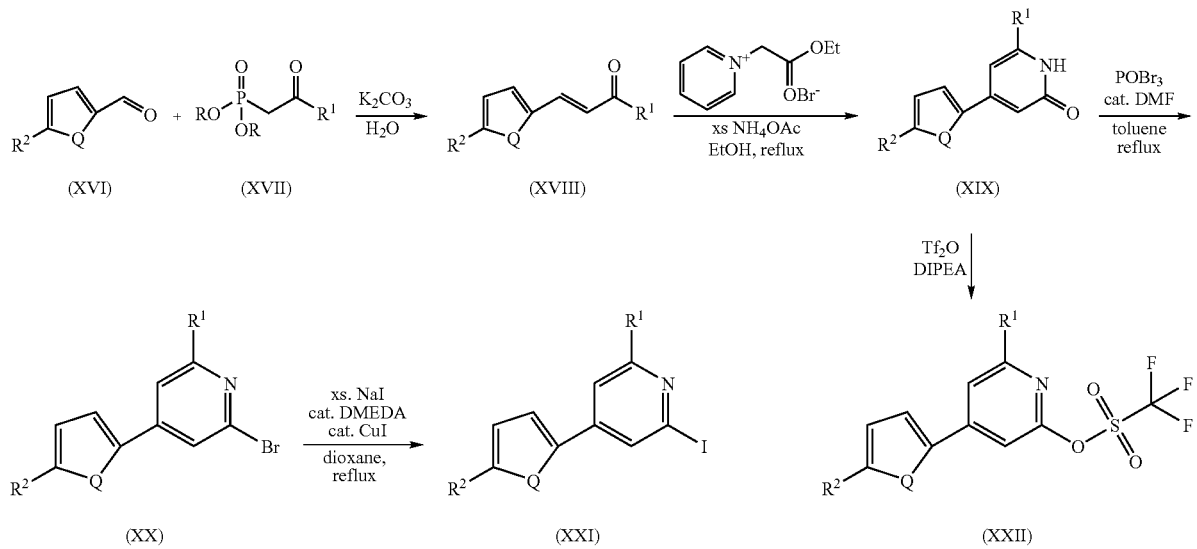

General Procedure Ia (for Bromides (XX) and Iodides (XXI)):

Step 1: To a vigorously stirred mixture of a carboxaldehyde compound of formula XVI (1.0 eq.), R1-containing phosphonate compound of formula XVII (1.2 eq.) (optionally with additional THF (20 ml/50 mmol aldehyde) at 23° C. (water-bath) was added a solution of potassium carbonate (2.0 eq.) in water (25 ml/50 mmol aldehyde) within 5 min and stirring was continued at 23° C. for 1.5 h. Diluted with EtOAc, THF and water, separated phases, washed organic layer with brine, reextracted combined organic layer once with EtOAc, dried combined organic layer over $Na_2SO_4$. Removal of the solvent in vacuum left the 3-aryl-prop-2-en-1-one-compound of formula XVIII, which was used without further purification.

Step 2: A stirred mixture of the 3-aryl-prop-2-en-1-one-compound of formula XVIII (1.0 eq.) and commercially available 1-ethoxycarbonylmethyl-pyridinium bromide [CAS-No. 17282-40-5] (1.1 eq.) and ammonium acetate (5 eq.) in a protic solvent (e.g. ethanol) was heated under reflux conditions for around 16 to 48 h. After cooling to room temperature, the mixture was diluted with 1M aqueous HCl (until pH 1 was achieved) and water, stirred for 30 min, the precipitate was filtered off, washed with water and was dried in air at 60° C. overnight to give the crude product, which was purified by trituration with diethyl ether/heptane to give the pure 4-aryl-2-pyridone of general formula XIX.

Step 3: To a stirred mixture of 4-aryl-2-pyridone of formula XIX (1.0 eq.) and phosphoryl bromide (1.0 to 3.0 eq.) in toluene is added DMF (0.3 to 0.4 eq.) and the reaction mixture is stirred at 105 to 115° C. for around 2 to 24 h, evaporated and ice-water is added. The precipitated solid is filtered off, dissolved in an organic solvent (e.g. tert-butyl methyl ether or ethyl acetate), the organic layer is washed with sat. $NaHCO_3$-sol., then with brine and finally dried over $MgSO_4$. Filtration and removal of the solvent in vacuum gave the crude material, which is either used without further purification or is purified by silica gel column chromatography (optionally followed by trituration with n-heptane) to give the pure 4-aryl-2-bromopyridines of formula XX.

Step 4: A stirred mixture of the 4-aryl-2-bromopyridines of formula XX (1.0 eq.), sodium iodide (2.0 eq.), copper(I) iodide (0.05 eq.) and N,N'-dimethylethylenediamine (DMEDA) (0.1 eq.) in 1,4-dioxane was heated at 110° C. for ca. 1-2 h according to a procedure in *J. Am. Chem. Soc.* 2002, 124(50), 14844. Cooled to rt, diluted with TBME or ethyl acetate, washed with diluted ammonia solution and brine, dried over $Na_2SO_4$. Removal of the solvent in vacuum left a light yellow solid, which could be used directly or triturated with n-heptane to give the pure 4-aryl-2-iodopyridines of formula XXI.

General Procedure Ib (for Triflates (XXII)):

Steps 1 and 2 are the same as in general procedure Ia.

Step 3: To a stirred mixture of 4-aryl-2-pyridone of formula XIX (1.0 eq.) in pyridine or ethyldiisopropyl amine/methylene chloride at temperatures between −15 and 0° C. was added trifluoromethanesulfonic anhydride (1.0 to 2.0 eq.) and stirring was continued at 0° C. for 0.5 to 16 h. Poured into ice-water, extracted with ethyl acetate, washed with ice cold 1 M sulfuric acid, saturated $NaHCO_3$-sol. and brine, dried over $Na_2SO_4$. Removal of the solvent in vacuum left the crude product as a brown solid which can be purified by silica gel column chromatography with heptane/EtOAc to give the pure triflates of general formula XXII.

Example A.1

2-Chloro-4-(5-chloro-thiophen-2-yl)-6-trifluoromethyl-pyrimidine 1) 4-(5-Chloro-thiophen-2-yl)-6-trifluoromethyl-1H-pyrimidin-2-one:

The compound was prepared from commercially available ethyl acetate, commercially available 5-acetyl-2-chlorothiophene (10.0 g, 0.06 mol) and urea according to the general procedure I. Obtained as a light yellow solid (10.6 g, 61%). MS (ISP) 281.0 [(M+H)$^+$]; mp 191° C.

2) The title compound was prepared from 4-(5-chloro-thiophen-2-yl)-6-trifluoromethyl-1H-pyrimidin-2-one (10.0 g, 35.6 mmol) and phosphoroxychloride (50 ml) according to the general procedure I. Obtained as a brown oil (10.4 g, 98%). MS (EI) 298.0, 299.9 [(M)$^+$].

Example A.2

2-Chloro-4-trifluoromethyl-6-(6-trifluoromethyl-pyridin-3-yl)-pyrimidine 1) 4-(6-Trifluoromethyl-pyridin-3-yl)-6-trifluoromethyl-1H-pyrimidin-2-one: The compound was prepared from commercially available ethyl trifluoroacetate, commercially available 1-[6-(trifluoromethyl)pyridin-3-yl]ethanone [CAS-No. 358780-14-0] and urea according to the general procedure I. Obtained as a light brown solid (6.98 g, 85%). MS (ISP) 310.2 [(M+H)$^+$]; mp 221° C.

2) The title compound was prepared from 4-(6-trifluoromethyl-pyridin-3-yl)-6-trifluoromethyl-1H-pyrimidin-2-one (6.87 g, 0.022 mol) and phosphoroxychloride (35 ml) according to the general procedure I. Obtained as a light brown solid (7.18 g, 99%). MS (ISP) 329.2 [(M+H)$^+$]; mp 87° C.

Example A.3

2-Chloro-4-difluoromethyl-6-(6-trifluoromethyl-pyridin-3-yl)-pyrimidine 1) 6-Difluoromethyl-4-(6-trifluoromethyl-pyridin-3-yl)-1H-pyrimidin-2-one: The compound was prepared from commercially available ethyl difluoroacetate, commercially available 1-[6-(trifluoromethyl)pyridin-3-yl]ethanone [CAS-No. 358780-14-0] and urea according to the general procedure I. Obtained as a light brown solid (6.37 g, 84%). MS (ISP) 292.1 [(M+H)$^+$]; mp 205.5° C.

2) The title compound was prepared from 6-difluoromethyl-4-(6-trifluoromethyl-pyridin-3-yl)-1H-pyrimidin-2-one (6.37 g, 0.022 mol) and phosphoroxychloride (34 ml) according to the general procedure I. Obtained as a brown oil (6.65 g, 98%). MS (ISP) 310.2 [(M+H)$^+$].

Example A.4

2-Chloro-4-methyl-6-(6-trifluoromethyl-pyridin-3-yl)-pyrimidine 1) 6-Methyl-4-(6-trifluoromethyl-pyridin-3-yl)-1H-pyrimidin-2-one: The compound was prepared from commercially available ethyl acetate, commercially available 1-[6-(trifluoromethyl)pyridin-3-yl]ethanone [CAS-No. 358780-14-0] and urea according to the general procedure I. Obtained as a light yellow solid (2.0 g, 31%). MS (ISP) 256.2 [(M+H)$^+$]; mp 250.5° C.

2) The title compound was prepared from 6-methyl-4-(6-trifluoromethyl-pyridin-3-yl)-1H-pyrimidin-2-one (2.0 g, 7.84 mmol) and phosphoroxychloride (12 ml) according to the general procedure I. Obtained as an orange solid (1.33 g, 62%). MS (ISP) 274.1 [(M+H)$^+$]; mp 123.5° C.

Example A.5

Trifluoro-methanesulfonic acid 6'-methyl-6-trifluoromethyl-[3,4']bipyridinyl-2'-yl ester 1) (E)-4-(6-Trifluoromethyl-pyridin-3-yl)-but-3-en-2-one: Prepared from commercially available 6-(trifluoromethyl)pyridine-3-carboxaldehyde [CAS-no. 386704-12-7] (5 g, 29 mmol), commercially available dimethyl-2-oxopropylphosphonate (4.8 mL, 35 mmol) and K$_2$CO$_3$ (7.97 g, 58 mmol) in water (60 mL) according to the general procedure Ia step 1. MS (ISP) 216.1 [(M+H)$^+$].

2) 6'-Methyl-6-trifluoromethyl-1'H-[3,4']bipyridinyl-2'-one: Prepared from the above described (E)-4-(6-trifluoromethyl-pyridin-3-yl)-but-3-en-2-one (6.6 g, 28 mmol, 91% purity), commercially available 1-ethoxycarbonylmethyl-pyridinium bromide [CAS-No. 17282-40-5] (7.58 g, 31 mmol) and ammonium acetate (10.8 g, 140 mmol) in EtOH (45 mL) according to general procedure Ia step 2. Obtained as a light yellow solid (2.0 g, 29%). MS (ISP) 255.1 [(M+H)$^+$].

3) The title compound was prepared from the above described 6'-methyl-6-trifluoromethyl-1'#H!-[3,4']bipyridinyl-2'-one (2.0 g, 8 mmol), diisopropylethylamine (5.4 ml, 32 mmol) and trifluoromethanesulfonic anhydride (3.2 mL, 19 mmol) according to the general procedure Ib step 3. Obtained as a light brown solid (1.75 g, 58%). MS (ISP) 387.1 [(M+H)$^+$].

Synthesis of Bromo- and chloro Derivatives

Coupling Partners

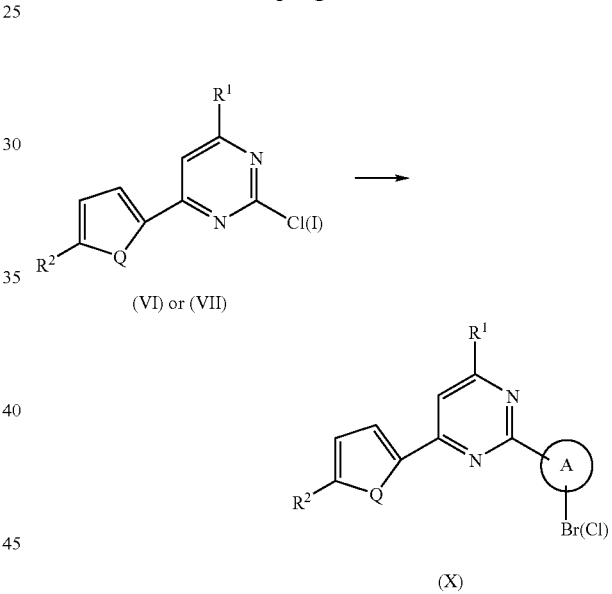

General Procedure IIa (C,N Connection)

A stirred mixture of a compound of formulae VI (1 eq), a imidazole derivative (1.5 eq) and potassium carbonate (1 eq) in an organic solvent (e.g. DMF) is heated at 130° C. for around 45 min, cooled, poured into water and extracted three times with ethyl acetate. The combined organic layers are washed two times with brine, dried (e.g. MgSO$_4$) and evaporated. The crude product is further purified by flash chromatography on silica gel (ethyl acetate/heptane) and crystallization (e.g. ethyl acetate/hexane) to give a compound of formulae X.

General Procedure IIb (C,C Connection A)

To a stirred mixture of a compound of formulae VI or VII (1 eq), a boronic acid derivative (1.1 eq) an tetrakis(triphenylphosphine)palladium (0.03 eq) in an organic solvent (e.g. 1,2-dimethoxy-ethane) is added at room temperature 1M sodium carbonate solution (2.5 eq), the reaction mixture is heated at 80° C. for around 23 h, cooled, poured into ice-water and extracted two times with ethyl acetate. The combined organic layers are washed two times with brine, dried (e.g. MgSO₄) and evaporated. The crude product is further purified by flash chromatography on silica gel (ethyl acetate/heptane) and crystallization (e.g. dichloromethane/hexane) to give a compound of formulae X.

General Procedure IIc (C,C Connection B)

To a stirred solution of commercially available 2-chloro-4-iodo-pyridine [CAS No. 153034-86-7] (1 eq) in an organic solvent (e.g. THF) is added at −65° C. iso-propylmagnesium chloride (2M in THF, 1 eq), the mixture is stirred at −45° C. for around 45 min. and zinc chloride (1M in THF, 1.1 eq) is added. The reaction mixture is stirred at room temperature for around 45 min, a compound of formulae VI or VII is added, the reaction mixture is stirred at 50° C. for around 16 h, cooled, poured into ice-saturated NaHCO₃ solution and extracted two times with ethyl acetate. The combined organic layers are washed with brine, dried (e.g. MgSO₄) and evaporated. The crude product is further purified by column chromatography on silica gel (toluene) to give a compound of formulae X.

Example B.1

4-(5-Chloro-thiophen-2-yl)-2-(4-iodo-imidazol-1-yl)-6-trifluoromethyl-pyrimidine The title compound was prepared from 2-chloro-4-(5-chloro-thiophen-2-yl)-6-trifluoromethyl-pyrimidine (example A.1) (1.2 g, 4.0 mmol) and commercially available 4-iodo-imidazole (0.85 g, 4.4 mmol) according to the general procedure Ia. Obtained as an off-white solid (1.78 g, 97%). MS (ISP) 457.0 [(M+H)⁺]; mp 251° C.

Example B.2

2-(3-Bromo-phenyl)-4-trifluoromethyl-6-(6-trifluoromethyl-pyridin-3-yl)-pyrimidine The title compound was prepared from 2-chloro-4-trifluoromethyl-6-(6-trifluoromethyl-pyridin-3-yl)-pyrimidine (example A.2) (1.50 g, 4.38 mmol) and commercially available 3-bromo-benzene-boronic acid (1.01 g, 5.03 mmol) according to the general procedure IIb. Obtained as a white solid (1.15 g, 56%). MS (EI) 448.0, 450.0 [(M)⁺]; mp 160° C.

Example B.3

2-(3-Bromo-phenyl)-4-(5-chloro-thiophen-2-yl)-6-trifluoromethyl-pyrimidine

The title compound was prepared from 2-chloro-4-(5-chloro-thiophen-2-yl)-6-trifluoromethyl-pyrimidine (example A.1) (1.2 g, 4.0 mmol) and commercially available 3-bromo-benzene-boronic acid (0.88 g, 4.38 mmol) according to the general procedure IIb. Obtained as a white solid (0.73 g, 43%). MS (EI) 419.9 [(M)⁺]; mp 124° C.

Example B.4

2-(2-Chloro-pyridin-4-yl)-4-trifluoromethyl-6-(6-trifluoromethyl-pyridin-3-yl)-pyrimidine The title compound was prepared from 2-chloro-4-trifluoromethyl-6-(6-trifluoromethyl-pyridin-3-yl)-pyrimidine (example A.2) (2.0 g, 6.1 mmol) and commercially available 2-chloro-pyridine-4-boronic acid (1.06 g, 6.74 mmol) according to the general procedure IIb. Obtained as a light brown solid (0.94 g, 38%). MS (ISN) 405.2 [(M−H)⁻]; mp 148.5° C.

Example B.5

2-(4-Iodo-imidazol-1-yl)-4-trifluoromethyl-6-(6-trifluoromethyl-pyridin-3-yl)-pyrimidine The title compound was prepared from 2-chloro-4-trifluoromethyl-6-(6-trifluoromethyl-pyridin-3-yl)-pyrimidine (example A.2) (1.31 g, 4.0 mmol) and commercially available 4-iodo-imidazole (0.85 g, 4.4 mmol) according to the general procedure Ia. Obtained as a light brown solid (1.84 g, 95%). MS (ISP) 486.9 [(M+H)⁺]; mp 179° C.

Example B.6

2-(3-Bromo-phenyl)-4-difluoromethyl-6-(6-trifluoromethyl-pyridin-3-yl)-pyrimidine The title compound was prepared from 2-chloro-4-difluoromethyl-6-(6-trifluoromethyl-pyridin-3-yl)-pyrimidine (example A.3) (2.0 g, 6.46 mmol) and commercially available 3-bromo-benzene-boronic acid (1.43 g, 7.12 mmol) according to the general procedure IIb. Obtained as a white solid (0.89 g, 32%). MS (ISP) 430.1 [(M+H)⁺]; mp 148.5° C.

Example B.7

2-(2-Chloro-pyridin-4-yl)-4-difluoromethyl-6-(6-trifluoromethyl-pyridin-3-yl)-pyrimidine The title compound was prepared from 2-chloro-4-difluoromethyl-6-(6-trifluoromethyl-pyridin-3-yl)-pyrimidine (example A.3) (2.0 g, 6.46 mmol) and commercially available 2-chloro-pyridine-4-boronic acid (1.12 g, 7.12 mmol) according to the general procedure IIb. Obtained as an off-white solid (0.6 g, 24%). MS (ISP) 387.1 [(M+H)⁺]; mp 185° C.

Example B.8

4-Difluoromethyl-2-(4-iodo-imidazol-1-yl)-6-(6-trifluoromethyl-pyridin-3-yl)-pyrimidine The title compound was prepared from 2-chloro-4-difluoromethyl-6-(6-trifluoromethyl-pyridin-3-yl)-pyrimidine (example A.3) (1.24 g, 4.0 mmol) and commercially available 4-iodo-imidazole (0.85 g, 4.4 mmol) according to the general procedure Ia. Obtained as a light brown solid (1.77 g, 95%). MS (ISP) 468.0 [(M+H)⁺]; mp 173° C.

Example B.9

2-(4-Iodo-imidazol-1-yl)-4-methyl-6-(6-trifluoromethyl-pyridin-3-yl)-pyrimidine

The title compound was prepared from 2-chloro-4-methyl-6-(6-trifluoromethyl-pyridin-3-yl)-pyrimidine (example A.4) (0.27 g, 1.0 mmol) and commercially available 4-iodo-imidazole (0.21 g, 1.1 mmol) according to the general procedure Ia. Obtained as a light brown solid (0.35 g, 81%). MS (ISP) 432.1 [(M+H)⁺]; mp 193.5° C.

Example B.10

2-(2-Chloro-pyridin-4-yl)-4-methyl-6-(6-trifluoromethyl-pyridin-3-yl)-pyrimidine The title compound was prepared from 2-chloro-4-methyl-6-(6-trifluoromethyl-pyridin-3-yl)-pyrimidine (example A.4) (0.63 g, 2.3 mmol) and commercially available 2-chloro-pyridine-4-boronic acid (0.4 g, 2.53 mmol) according to the general procedure IIb. Obtained as a light yellow solid (0.53 g, 65%). MS (ISP) 351.1 [(M+H)⁺]; mp 183.5° C.

Example B.11

2-(3-Bromo-phenyl)-4-methyl-6-(6-trifluoromethyl-pyridin-3-yl)-pyrimidine

The title compound was prepared from 2-chloro-4-methyl-6-(6-trifluoromethyl-pyridin-3-yl)-pyrimidine (example A.4) (0.41 g, 1.5 mmol) and commercially available 3-bromo-benzene-boronic acid (0.33 g, 1.64 mmol) according to the general procedure IIb. Obtained as a light yellow solid (0.30 g, 51%). MS (ISP) 394.0 [(M+H)⁺]; mp 130° C.

Example B.12

6'-(3-Bromo-phenyl)-2'-methyl-6-trifluoromethyl-[3,4']bipyridinyl

The title compound was prepared from trifluoro-methane-sulfonic acid 6'-methyl-6-trifluoromethyl-[3,4']bipyridinyl-2'-yl ester (example A.5) (0.773 g, 2.0 mmol) and commercially available 3-bromo-benzene-boronic acid (0.43 g, 2.1 mmol) according to the general procedure IIb. Obtained as a white solid (0.69 g, 88%). MS (ISP) 393.1 [(M+H)⁺] and 395.1 [(M+2+H)⁺].

Example C.1

N-tert-Butyl-5-(4,4,5,5-tetramethyl-1,3,2-dioxaborolan-2-yl)-thiophene-2-sulfonamide To a stirred solution of commercially available 5-bromo-N-tert-butyl-thiophene-2-sulfonamide (16.9 g, 56.7 mmol) and commercially available triisopropyl borate (39.4 g, 0.21 mol) in THF (500 ml) was added dropwise at −78° C. n-butyllithium (1.6 M in hexane, 131 ml, 0.21 mol) in a way that the temperature did not exceed −65° C. The mixture was allowed to stir for 3 h at −78° C. and afterwards water (500 ml) was added dropwise at −20° C. The layers were separated, the water phase was extracted with diethylether (4×200 ml) and afterwards 2N HCl was added (120 ml). The acidic water layer was extracted with ethyl acetate (3×200 ml), the combined organic layers were dried (MgSO₄) and evaporated to yield a light brown gum (12.3 g, 83%), which was dissolved in toluene (400 ml). Pinakol (16.6 g, 0.14 mol) and p-toluenesulfonic acid (0.27 g, 1.41 mmol) was added, the reaction mixture was heated under reflux conditions for 3 h and evaporated to yield a light brown oil. Hexane (50 ml) was added and the mixture was stirred at room temperature for 30 min. The precipitate was collected by filtration, washed with hexane and dried to yield the title compound as an off-white solid (9.3 g, 57%). MS (EI) 345.2 [(M)⁺]; mp 127° C.

Example C.2

N-tert-Butyl-3-(6-tributylstannanyl-pyridin-2-yl)-benzenesulfonamide

Step 1) 3-(6-Bromo-pyridin-2-yl)-N-tert-butyl-benzenesulfonamide: A mixture of commercially available 3-(tert-butylsulfamoyl)-benzeneboronic acid (5.142 g, 20 mmol), commercially available 2,6-dibromopyridine (14.2 g, 60 mmol) and Pd(PPh₃)₄ (1.156 g, 5 mol %) in DME (80 ml) and aqueous sodium carbonate (1 M, 40 ml, 40 mmol) was stirred at 90° C. under argon atmosphere for 18 h. The reaction mixture was extracted with water and ethyl acetate, the organic layers dried over MgSO₄, filtered and the solvents evaporated. The crude product was purified by flash chromatography with n-heptane/ethyl acetate to give the 3-(6-bromo-pyridin-2-yl)-N-tert-butyl-benzenesulfonamide (6.60 g, 89%) as a yellow solid. MS (ISP) 369.1 [(M+H)⁺] and 371.0 [(M+2+H)⁺].

Step 2) A mixture of the above described 3-(6-bromo-pyridin-2-yl)-N-tert-butyl-benzenesulfonamide (4.6 g, 12 mmol), hexabutyldistannane (9.9 ml, 19 mmol) and Pd(PPh₃)₄ (144 mg, 1 mol %) in toluene (135 ml) was stirred at 80° C. for 18 h. The solvents were evaporated and the crude product directly purified by flash chromatography with n-heptane/ethyl acetate to give the title compound (1.66 g, 23%) as a yellow oil. MS (ISP) 580.7 [(M+H)⁺].

General Procedure III

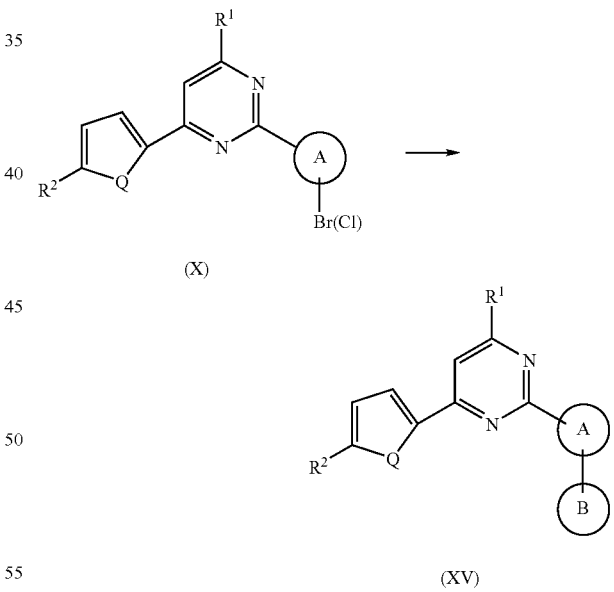

To a stirred mixture of a compound of formulae X (1 eq), a boronic acid derivative (1 eq) and tetrakis(triphenylphosphine)palladium (0.1 eq) in an organic solvent (e.g. dioxane) is added at room temperature 1M sodium carbonate solution (2 eq), the reaction mixture is heated under reflux conditions for around 18 h, cooled, poured into ice-water and extracted two times with ethyl acetate. The combined organic layers are washed two times with brine, dried (e.g. MgSO₄) and evaporated. The crude product is further purified by column chromatography on silica gel (e.g. MeCl₂(MeOH/NH₄OH 20:1:

0.1) and crystallization (e.g. dichloro methane/MeOH/hexane) to give a compound of formulae XV.

General Procedure IV

The general procedure IV allows the synthesis of pyrimidines of formula XV from 3-aryl-2-alkyn-1-ones of formula XXVI and amidines of formula XXX as described in *Synlett* 2003, (2), 259-261. A compound of formula XXIII, wherein the halide is preferably bromide or iodide, can be reacted with an 2-alkyn-1-ol of formula XXIV under so called Sonogashira conditions as for example described in *Journal of Organic Chemistry* 1998, 63(23), 8551-8553. The resulting 3-aryl-2-alkyn-1-ol of formula XXV can be oxidized to the corresponding 3-aryl-2-alkyn-1-one of formula XXVI by many methods known to someone skilled in the art, e.g. by so called Jones oxidation with chromium(VI) oxide ($CrO_3$) in a mixture of aqueous sulfuric acid and acetone, Dess-Martin Periodinane (DMP) in methylene chloride, so called Swern oxidation (oxalyl chloride, dimethyl sulfoxide, triethylamine in methylene chloride, pyridinium chlorochromate (PCC) or pyridinium dichromate (PDC) in methylene chloride, manganese(IV) oxide ($MnO_2$) in methylene chloride or acetone.

The nitrile of formula XXVIII can be prepared by someone skilled in the art from the corresponding bromides or iodides of formula XXVII by either palladium-catalyzed reaction with zinc or potassium cyanide or by reaction with copper(I) cyanide (CuCN). The amidoximes of the formula XXIX can be prepared by someone skilled in the art by reaction a nitrile of formula XXVIII with hydroxylamine hydrochloride in aqueous methanol or ethanol in the presence of a base like e.g. sodium or potassium carbonate at temperatures between 23 and 80° C. The amidines of formula XXX can be prepared by reduction of the amidoximes of formula XXIX by methods known to someone skilled in the art, like e.g. catalytic hydrogenation in the presence of a palladium-catalyst, like e.g. palladium on carbon, or rhodium-catalyst, like e.g. rhodium on alumina, or nickel-catalyst, like e.g. Raney-nickel, in protic solvents like e.g. ethanol, methanol or acetic acid (preferably in the presence of acetic anhydride as described in *Synthetic Communications* 1998, 28(23), 4419-4429).

All detailed procedures for the respective compounds can be found in the description of the examples.

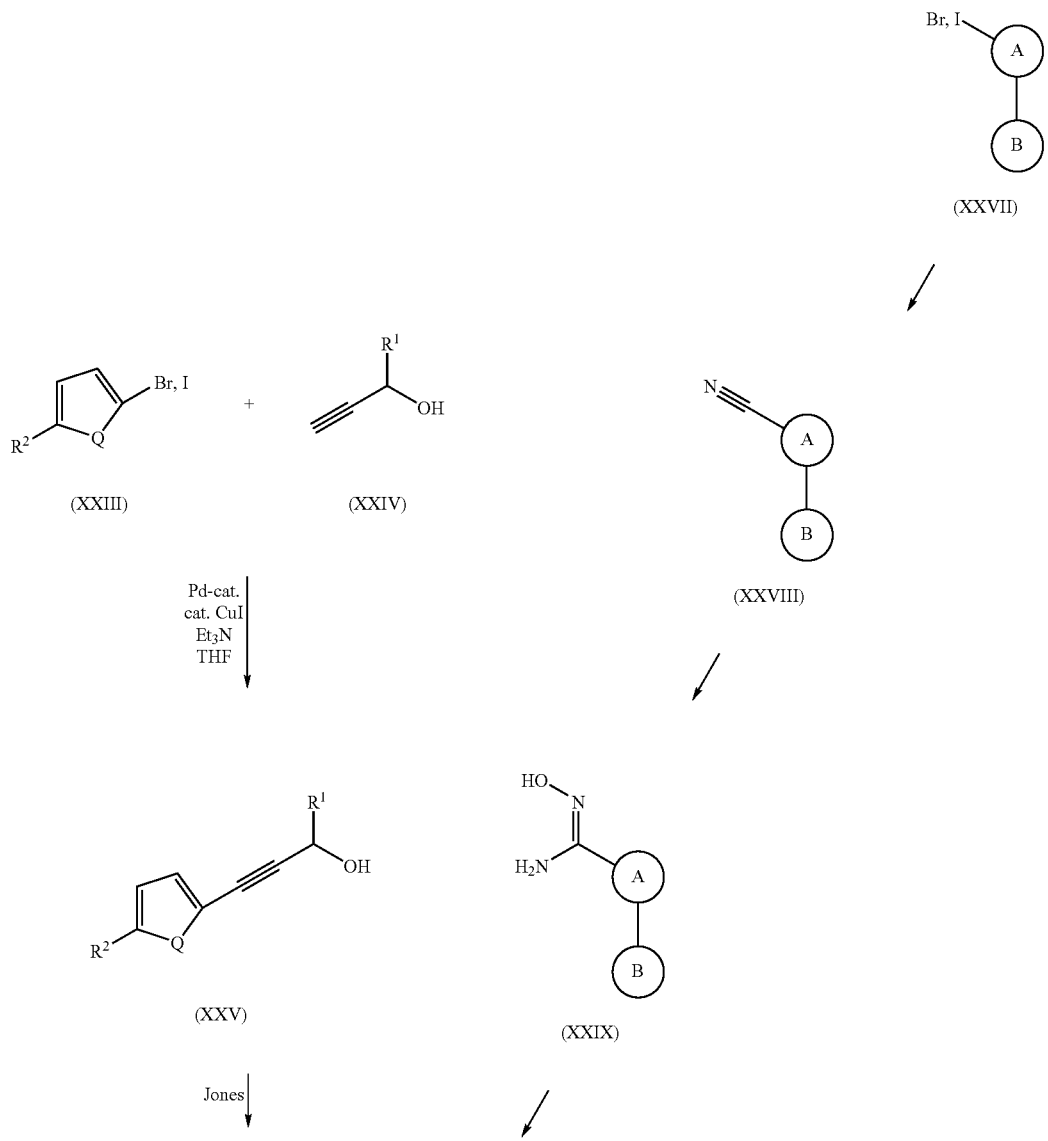

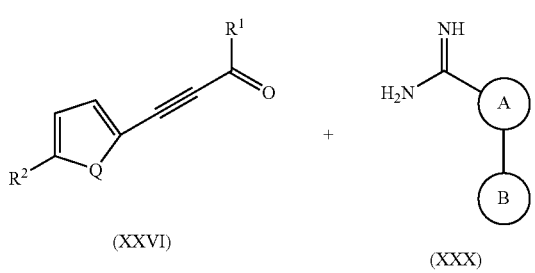

(XXVI) + (XXX) → (XV)

Example 1

3-{1-[4-(5-Chloro-thiophen-2-yl)-6-trifluoromethyl-pyrimidin-2-yl]-1H-imidazol-4-yl}-benzenesulfonamide 1) N-tert-Butyl-3-{1-[4-(5-chloro-thiophen-2-yl)-6-trifluoromethyl-pyrimidin-2-yl]-1H-imidazol-4-yl}-benzenesulfonamide was prepared from 4-(5-chloro-thiophen-2-yl)-2-(4-iodo-imidazol-1-yl)-6-trifluoromethyl-pyrimidine (example B.1) (0.46 g, 1.0 mmol) and commercially available 3-(tert.-butylsulfamoyl)-phenylboronic acid (0.28 g, 1.1 mmol) according to the general procedure III. Obtained as a light yellow solid (0.3 g) which was subsequently deprotected.

2) To a cooled and stirred solution of N-tert-butyl-3-{1-[4-(5-chloro-thiophen-2-yl)-6-trifluoromethyl-pyrimidin-2-yl]-1H-imidazol-4-yl}-benzenesulfonamide (0.3 g) in dichloromethane (6 ml) was added TFA (6 ml) and the reaction mixture was allowed to stir at room temperature for 15 h. The mixture was evaporated to dryness, poured into 2N NaHCO$_3$ solution (20 ml) and extracted with ethyl acetate (2×30 ml). The combined organic layers were washed with brine (20 ml), dried (MgSO$_4$) and evaporated. Further purification by flash chromatography on silica gel (ethyl acetate/heptane) and crystallization (dichloromethane/MeOH/hexane) yielded the title compound as an off-white solid (0.08 g, 16%). MS (ISP) 485.9 [(M+H)$^+$]; mp 189° C.

Example 2

3'-[4-Trifluoromethyl-6-(6-trifluoromethyl-pyridin-3-yl)-pyrimidin-2-yl]-biphenyl-3-sulfonic acid amide 1) 3'-[4-Trifluoromethyl-6-(6-trifluoromethyl-pyridin-3-yl)-pyrimidin-2-yl]-biphenyl-3-sulfonic acid tert-butylamide was prepared from 2-(3-bromo-phenyl)-4-trifluoromethyl-6-(6-trifluoromethyl-pyridin-3-yl)-pyrimidine (example B.2) (0.448 g, 1.0 mmol) and commercially available 3-(tert.-butylsulfamoyl)-phenylboronic acid (0.31 g, 1.2 mmol) according to the general procedure III. Obtained as light yellow solid (0.56 g), which was subsequently deprotected.

2) To a cooled and stirred solution of 3'-[4-trifluoromethyl-6-(6-trifluoromethyl-pyridin-3-yl)-pyrimidin-2-yl]-biphenyl-3-sulfonic acid tert-butylamide (0.56 g) in dichloromethane (6 ml) was added TFA (6 ml) and the reaction mixture was allowed to stir at room temperature for 15 h. The mixture was evaporated to dryness, poured into 2N Na$_2$CO$_3$ solution (25 ml) and extracted with ethyl acetate (3×50 ml). The combined organic layers were washed with brine (50 ml), dried (MgSO$_4$) and evaporated. Further purification by crystallization (ethyl acetate/heptane) yielded the title compound as a white solid (0.39 g, 74%). MS (ISP) 525.2 [(M+H)$^+$]; mp 211° C.

Example 3

5-{3-[4-Trifluoromethyl-6-(6-trifluoromethyl-pyridin-3-yl)-pyrimidin-2-yl]-phenyl}-thiophene-2-sulfonic acid amide 1) N-tert-Butyl-5-{3-[4-trifluoromethyl-6-(6-trifluoromethyl-pyridin-3-yl)-pyrimidin-2-yl]-phenyl}-thiophene-2-sulfonic acid amide was prepared from 2-(3-bromo-phenyl)-4-trifluoromethyl-6-(6-trifluoromethyl-pyridin-3-yl)-pyrimidine (example B.2) (0.448 g, 1.0 mmol) and N-tert-butyl-5-(4,4,5,5-tetramethyl-1,3,2-dioxaborolan-2-yl)-thiophene-2-sulfonamide (example C.1) (0.414 g, 1.2 mmol) according to the general procedure III. Obtained as an off-white solid (0.45 g), which was subsequently deprotected.

2) To a cooled and stirred solution of N-tert-butyl-5-{3-[4-trifluoromethyl-6-(6-trifluoromethyl-pyridin-3-yl)-pyrimidin-2-yl]-phenyl}-thiophene-2-sulfonic acid amide (0.45 g) in dichloromethane (6 ml) was added TFA (6 ml) and the reaction mixture was allowed to stir at room temperature for 15 h. The mixture was evaporated to dryness, poured into 2N Na$_2$CO$_3$ solution (25 ml) and extracted with ethyl acetate (3×50 ml). The combined organic layers were washed with brine (50 ml), dried (MgSO$_4$) and evaporated. Further purification by flash chromatography on silica gel (ethyl acetate/heptane) and crystallization (ethyl acetate/heptane) yielded the title compound as a light yellow solid (0.2 g, 38%). MS (ISP) 531.0 [(M+H)$^+$]; mp 250.5° C.

Example 4

3'-[4-(5-Chloro-thiophen-2-yl)-6-trifluoromethyl-pyrimidin-2-yl]-biphenyl-3-sulfonic acid amide 1) 3'-[4-(5-Chloro-thiophen-2-yl)-6-trifluoromethyl-pyrimidin-2-yl]-biphenyl-3-sulfonic acid tert-butylamide was prepared from 2-(3-bromo-phenyl)-4-(5-chloro-thiophen-2-yl)-6-trifluoromethyl-pyrimidine (example B.3) (0.42 g, 1.0 mmol) and commercially available 3-(tert.-butylsulfamoyl)-phenylboronic acid (0.334 g, 1.3 mmol) according to the general procedure III. Obtained as an off-white solid (0.22 g), which was subsequently deprotected.

2) To a cooled and stirred solution of 3'-[4-(5-chloro-thiophen-2-yl)-6-trifluoromethyl-pyrimidin-2-yl]-biphenyl-3-sulfonic acid tert-butylamide (0.22 g) in dichloromethane (5 ml) was added TFA (5 ml) and the reaction mixture was allowed to stir at room temperature for 15 h. The mixture was evaporated, poured into saturated NaHCO₃ solution (20 ml) and extracted with ethyl acetate (2×30 ml). The combined organic layers were washed with brine (20 ml), dried (MgSO₄) and evaporated. Further purification by flash chromatography on silica gel (ethyl acetate/heptane) and crystallization (MeOH) yielded the title compound as a light yellow solid (0.13 g, 27%). MS (ISN) 494.3 [(M−H)⁻]; mp 226.5° C.

Example 5

5-{3-[4-(5-Chloro-thiophen-2-yl)-6-trifluoromethyl-pyrimidin-2-yl]-phenyl}-pyridin-2-ylamine The title compound was prepared from 2-(3-bromo-phenyl)-4-(5-chloro-thiophen-2-yl)-6-trifluoromethyl-pyrimidine (example B.3) (0.25 g, 0.6 mmol) and commercially available 2-amino-5-(4,4,5,5-tetramethyl-1,3,2-dioxaborolan-2-yl)pyridine (0.157 g, 0.71 mmol) according to the general procedure III. Obtained as a yellow solid (0.083 g, 32%). MS (ISP) 433.2 [(M+H)⁺]; mp 99° C.

Example 6

5{-3-[4-(5-Chloro-thiophen-2-yl)-6-trifluoromethyl-pyrimidin-2-yl]-phenyl}-pyridin-2-ylamine The title compound was prepared from 2-(3-bromo-phenyl)-4-(5-chloro-thiophen-2-yl)-6-trifluoromethyl-pyrimidine (example B.3) (0.31 g, 0.74 mmol) and commercially available 2-amino-5-(4,4,5,5-tetramethyl-1,3,2-dioxaborolan-2-yl)pyridine (0.18 g, 0.81 mmol) according to the general procedure III. Obtained as a light yellow solid (0.075 g, 23%). MS (ISP) 434.2 [(M+H)⁺]; mp 228° C.

Example 7

5-{3-[4-(5-Chloro-thiophen-2-yl)-6-trifluoromethyl-pyrimidin-2-yl]-phenyl}-thiophene-2-sulfonic acid amide 1) 5-{3-[4-(5-Chloro-thiophen-2-yl)-6-trifluoromethyl-pyrimidin-2-yl]-phenyl}-thiophene-2-sulfonic acid tert-butylamide was prepared from 2-(3-bromo-phenyl)-4-(5-chloro-thiophen-2-yl)-6-trifluoromethyl-pyrimidine (example B.3) (0.31 g, 0.74 mmol) and N-tert-butyl-5-(4,4,5,5-tetramethyl-1,3,2-dioxaborolan-2-yl)-thiophene-2-sulfonamide (example C.1) (0.28 g, 0.81 mmol) according to the general procedure III. Obtained as light yellow oil (0.23 g), which was subsequently deprotected.

2) To a cooled and stirred solution of 5-{3-[4-(5-chloro-thiophen-2-yl)-6-trifluoromethyl-pyrimidin-2-yl]-phenyl}-thiophene-2-sulfonic acid tert-butylamide (0.23 g) in dichloromethane (5 ml) was added TFA (5 ml) and the reaction mixture was allowed to stir at room temperature for 15 h. The mixture was evaporated, and purified by flash chromatography on silica gel (ethyl acetate/heptane) and crystallization (MeOH, dichloromethane, hexane) yielded the title compound as a light yellow solid (0.084 g, 23%). MS (ISP) 502.0 [(M+H)⁺]; mp 233° C.

Example 8

4-[4-Trifluoromethyl-6-(6-trifluoromethyl-pyridin-3-yl)-pyrimidin-2-yl]-[2,3']bipyridinyl-6'-ylamine The title compound was prepared from 2-(2-chloro-pyridin-4-yl)-4-trifluoromethyl-6-(6-trifluoromethyl-pyridin-3-yl)-pyrimidine (example B.4) (0.2 g, 0.5 mmol) and commercially available 2-amino-5-(4,4,5,5-tetramethyl-1,3,2-dioxaborolan-2-yl)pyridine (0.13 g, 0.6 mmol) according to the general procedure III. Obtained as a yellow solid (0.1 g, 43%). MS (ISP) 463.1 [(M+H)⁺]; mp 261.5° C.

Example 9

3-{4-[4-Trifluoromethyl-6-(6-trifluoromethyl-pyridin-3-yl)-pyrimidin-2-yl]-pyridin-2-yl}-benzenesulfonamide 1) 3-{4-[4-Trifluoromethyl-6-(6-trifluoromethyl-pyridin-3-yl)-pyrimidin-2-yl]-pyridin-2-yl}-benzenesulfonic acid tert-butylamide was prepared from 2-(2-chloro-pyridin-4-yl)-4-trifluoromethyl-6-(6-trifluoromethyl-pyridin-3-yl)-pyrimidine (example B.4) (0.81 g, 2.0 mmol) and commercially available 3-(tert.-butylsulfamoyl)-phenylboronic acid (0.62 g, 2.4 mmol) according to the general procedure III. Obtained as off-white solid (0.71 g), which was subsequently deprotected.

2) To a cooled and stirred solution of 3-{4-[4-trifluoromethyl-6-(6-trifluoromethyl-pyridin-3-yl)-pyrimidin-2-yl]-pyridin-2-yl}-benzenesulfonic acid tert-butylamide (0.71 g) in dichloromethane (12 ml) was added TFA (12 ml) and the reaction mixture was allowed to stir at room temperature for 15 h. The mixture was evaporated to dryness, poured into 2N Na₂CO₃ solution (25 ml) and extracted with ethyl acetate (3×50 ml). The combined organic layers were washed with brine (50 ml), dried (MgSO₄) and evaporated. Further purification by crystallization (ethyl acetate/heptane) yielded the title compound as a white solid (0.51 g, 49%). MS (ISP) 526.2 [(M+H)⁺]; mp 258° C.

Example 10

5-{4-[4-Trifluoromethyl-6-(6-trifluoromethyl-pyridin-3-yl)-pyrimidin-2-yl]-pyridin-2-yl}-thiophene-2-sulfonic acid amide 1) 5-{4-[4-Trifluoromethyl-6-(6-trifluoromethyl-pyridin-3-yl)-pyrimidin-2-yl]-pyridin-2-yl}-thiophene-2-sulfonic-acid tert-butylamide was prepared from 2-(2-chloro-pyridin-4-yl)-4-trifluoromethyl-6-(6-trifluoromethyl-pyridin-3-yl)-pyrimidine (example B.4) (0.405 g, 1.0 mmol) and N-tert-butyl-5-(4,4,5,5-tetramethyl-1,3,2-dioxaborolan-2-yl)-thiophene-2-sulfonamide (example C.1) (0.414 g, 1.2 mmol) according to the general procedure III. Obtained as an off-white solid (0.44 g), which was subsequently deprotected.

2) To a cooled and stirred solution of 5-{4-[4-trifluoromethyl-6-(6-trifluoromethyl-pyridin-3-yl)-pyrimidin-2-yl]-pyridin-2-yl}-thiophene-2-sulfonic-acid tert-butylamide (0.44 g) in dichloromethane (6 ml) was added TFA (6 ml) and the reaction mixture was allowed to stir at room temperature for 15 h. The mixture was evaporated to dryness, poured into 2N Na₂CO₃ solution (25 ml) and extracted with ethyl acetate (3×50 ml). The combined organic layers were washed with brine (50 ml), dried (MgSO₄) and evaporated. Further purification by flash chromatography on silica gel (ethyl acetate/heptane) and crystallization (MeOH, dichloromethane) yielded the title compound as a white solid (0.11 g, 21%). MS (ISP) 532.0 [(M+H)⁺]; mp 262.5° C.

Example 11

N-Propionyl-3-{4-[4-trifluoromethyl-6-(6-trifluoromethyl-pyridin-3-yl)-pyrimidin-2-yl]-pyridin-2-yl}-benzenesulfonamide A mixture of 3-{4-[4-trifluoromethyl-6-(6-trifluoromethyl-pyridin-3-yl)-pyrimidin-2-yl]-pyridin-2-yl}-benzenesulfonamide (example 9) (0.3 g, 0.57 mmol) and propionic acid anhydride (0.75 ml) was stirred at 160° C. for 29 h. Hexane (15 ml) was added drop wise to the mixture at a temperature of 80° C. while the product precipitated. Ethyl acetate (2 ml) was added and the mixture was allowed to stir at RT for 1 h. The precipitate was collected by filtration and dried to yield the title compound (0.23 g, 69%) as a white solid. MS (ISP) 582.1 [(M+H))$^+$]; mp 242° C.

Example 12

5-{3-[4-Trifluoromethyl-6-(6-trifluoromethyl-pyridin-3-yl)-pyrimidin-2-yl]-phenyl}-pyridin-2-ylamine The title compound was prepared from 2-(3-bromo-phenyl)-4-trifluoromethyl-6-(6-trifluoromethyl-pyridin-3-yl)-pyrimidine (example B.2) (0.22 g, 0.5 mmol) and commercially available 2-amino-5-(4,4,5,5-tetramethyl-1,3,2-dioxaborolan-2-yl)pyridine (0.13 g, 0.6 mmol) according to the general procedure III. Obtained as a yellow solid (0.2 g, 87%). MS (ISP) 462.2 [(M+H)$^+$]; mp 244° C.

Example 13

5-{1-[4-Trifluoromethyl-6-(6-trifluoromethyl-pyridin-3-yl)-pyrimidin-2-yl]-1H-imidazol-4-yl}-pyridin-2-ylamine The title compound was prepared from 2-(4-iodo-imidazol-1-yl)-4-trifluoromethyl-6-(6-trifluoromethyl-pyridin-3-yl)-pyrimidine (example B.5) (0.485 g, 1.0 mmol) and commercially available 2-amino-5-(4,4,5,5-tetramethyl-1,3,2-dioxaborolan-2-yl)pyridine (0.264 g, 1.2 mmol) according to the general procedure III. Obtained as a yellow solid (0.03 g, 7%). MS (ISP) 452.1 [(M+H)$^+$]; mp 259° C.

Example 14

5-{1-[4-Difluoromethyl-6-(6-trifluoromethyl-pyridin-3-yl)-pyrimidin-2-yl]-1H-imidazol-4-yl}-pyridin-2-ylamine The title compound was prepared from 2-(4-iodo-imidazol-1-yl)-4-difluoromethyl-6-(6-trifluoromethyl-pyridin-3-yl)-pyrimidine (example B.8) (0.47 g, 1.0 mmol) and commercially available 2-amino-5-(4,4,5,5-tetramethyl-1,3,2-dioxaborolan-2-yl)pyridine (0.264 g, 1.2 mmol) according to the general procedure III. Obtained as a yellow solid (0.066 g, 15%). MS (ISP) 434.2 [(M+H)$^+$]; mp 258° C.

Example 15

3'-[4-Difluoromethyl-6-(6-trifluoromethyl-pyridin-3-yl)-pyrimidin-2-yl]-biphenyl-3-sulfonic acid amide 1) 3'-[4-Difluoromethyl-6-(6-trifluoromethyl-pyridin-3-yl)-pyrimidin-2-yl]-biphenyl-3-sulfonic acid tert-butylamide was prepared from 2-(3-bromo-phenyl)-4-difluoromethyl-6-(6-trifluoromethyl-pyridin-3-yl)-pyrimidine (example B.6) (0.43 g, 1.0 mmol) and commercially available 3-(tert.-butylsulfamoyl)-phenylboronic acid (0.31 g, 1.2 mmol) according to the general procedure III. Obtained as light yellow solid (0.62 g), which was subsequently deprotected.

2) To a cooled and stirred solution of 3'-[4-difluoromethyl-6-(6-trifluoromethyl-pyridin-3-yl)-pyrimidin-2-yl]-biphenyl-3-sulfonic acid tert-butylamide (0.56 g) in dichloromethane (7 ml) was added TFA (7 ml) and the reaction mixture was allowed to stir at room temperature for 15 h. The mixture was evaporated to dryness, poured into 2N Na$_2$CO$_3$ solution (25 ml) and extracted with ethyl acetate (3×50 ml). The combined organic layers were washed with brine (50 ml), dried (MgSO$_4$) and evaporated. Further purification by crystallization (ethyl acetate/heptane) yielded the title compound as a white solid (0.41 g, 81%). MS (ISP) 507.2 [(M+H)$^+$]; mp 222° C.

Example 16

3-{4-[4-Difluoromethyl-6-(6-trifluoromethyl-pyridin-3-yl)-pyrimidin-2-yl]-pyridin-2-yl}-benzenesulfonamide 1) 3-{4-[4-Difluoromethyl-6-(6-trifluoromethyl-pyridin-3-yl)-pyrimidin-2-yl]-pyridin-2-yl}-benzenesulfonic acid tert-butylamide was prepared from 2-(2-chloro-pyridin-4-yl)-4-difluoromethyl-6-(6-trifluoromethyl-pyridin-3-yl)-pyrimidine (example B.7) (0.19 g, 0.5 mmol) and commercially available 3-(tert.-butylsulfamoyl)-phenylboronic acid (0.15 g, 0.6 mmol) according to the general procedure III. Obtained as off-white solid (0.16 g), which was subsequently deprotected.

2) To a cooled and stirred solution of 3-{4-[4-difluoromethyl-6-(6-trifluoromethyl-pyridin-3-yl)-pyrimidin-2-yl]-pyridin-2-yl}-benzenesulfonic acid tert-butylamide (0.16 g) in dichloromethane (4 ml) was added TFA (4 ml) and the reaction mixture was allowed to stir at room temperature for 15 h. The mixture was evaporated to dryness, poured into 2N Na$_2$CO$_3$ solution (25 ml) and extracted with ethyl acetate (3×50 ml). The combined organic layers were washed with brine (50 ml), dried (MgSO$_4$) and evaporated. Further purification by column chromatography on silica gel (dichloromethane/MeOH/NH$_4$OH 16:1:0.1) and trituration (diethyl ether) yielded the title compound as a white solid (0.056 g, 22%). MS (ISP) 508.1 [(M+H)$^+$]; mp 264.5° C.

Example 17

5-{4-[4-Difluoromethyl-6-(6-trifluoromethyl-pyridin-3-yl)-pyrimidin-2-yl]-pyridin-2-yl}-thiophene-2-sulfonic acid amide 1) 5-{4-[4-Difluoromethyl-6-(6-trifluoromethyl-pyridin-3-yl)-pyrimidin-2-yl]-pyridin-2-yl}-thiophene-2-sulfonic-acid tert-butylamide was prepared from 2-(2-chloro-pyridin-4-yl)-4-difluoromethyl-6-(6-trifluoromethyl-pyridin-3-yl)-pyrimidine (example B.7) (0.39 g, 1.0 mmol) and N-tert-butyl-5-(4,4,5,5-tetramethyl-1,3,2-dioxaborolan-2-yl)-thiophene-2-sulfonamide (example C.1) (0.414 g, 1.2 mmol) according to the general procedure III. Obtained as an off-white solid (0.36 g), which was subsequently deprotected.

2) To a cooled and stirred solution of 5-{4-[4-difluoromethyl-6-(6-trifluoromethyl-pyridin-3-yl)-pyrimidin-2-yl]-pyridin-2-yl}-thiophene-2-sulfonic-acid tert-butylamide (0.36 g) in dichloromethane (6 ml) was added TFA (6 ml) and the reaction mixture was allowed to stir at room temperature for 15 h. The mixture was evaporated to dryness, poured into 2N Na$_2$CO$_3$ solution (25 ml) and extracted with ethyl acetate (3×50 ml). The combined organic layers were washed with brine (50 ml), dried (MgSO$_4$) and evaporated. Further purification by flash chromatography on silica gel (ethyl acetate/heptane) and crystallization (MeOH, dichloromethane) yielded the title compound as a white solid (0.11 g, 21%). MS (ISP) 514.2 [(M+H)$^+$]; mp 269.5° C.

Example 18

5-{3-[4-Difluoromethyl-6-(6-trifluoromethyl-pyridin-3-yl)-pyrimidin-2-yl]-phenyl}-thiophene-2-sulfonic acid amide 1) N-tert-Butyl-5-{3-[4-difluoromethyl-6-(6-trifluoromethyl-pyridin-3-yl)-pyrimidin-2-yl]-phenyl}-thiophene-2-sulfonic acid amide was prepared from 2-(3-bromo-phenyl)-4-difluoromethyl-6-(6-trifluoromethyl-pyridin-3-yl)-pyrimidine (example B.6) (0.43 g, 1.0 mmol) and N-tert-butyl-5-(4,4,5,5-tetramethyl-1,3,2-dioxaborolan-2-yl)-thiophene-2-sulfonamide (example C.1) (0.414 g, 1.2 mmol) according to the general procedure III. Obtained as an off-white solid (0.46 g), which was subsequently deprotected.

2) To a cooled and stirred solution of N-tert-butyl-5-{3-[4-difluoromethyl-6-(6-trifluoromethyl-pyridin-3-yl)-pyrimidin-2-yl]-phenyl}-thiophene-2-sulfonic acid amide (0.46 g) in dichloromethane (7 ml) was added TFA (7 ml) and the reaction mixture was allowed to stir at room temperature for 15 h. The mixture was evaporated to dryness, poured into 2N Na$_2$CO$_3$ solution (25 ml) and extracted with ethyl acetate (3×50 ml). The combined organic layers were washed with brine (50 ml), dried (MgSO$_4$) and evaporated. Further purification by flash chromatography on silica gel (ethyl acetate/heptane) and crystallization (dichloromethane/MeOH) yielded the title compound as a white solid (0.16 g, 31%). MS (ISP) 513.2 [(M+H)$^+$]; mp 245.5° C.

Example 19

3-{1-[4-Difluoromethyl-6-(6-trifluoromethyl-pyridin-3-yl)-pyrimidin-2-yl]-1H-imidazol-4-yl}-benzenesulfonamide 1) 3-{1-[4-Difluoromethyl-6-(6-trifluoromethyl-pyridin-3-yl)-pyrimidin-2-yl]-1H-imidazol-4-yl}-benzenesulfonic acid tert-butylamide was prepared from 2-(4-iodo-imidazol-1-yl)-4-difluoromethyl-6-(6-trifluoromethyl-pyridin-3-yl)-pyrimidine (example B.8) (0.47 g, 1.0 mmol) and commercially available 3-(tert.-butylsulfamoyl)-phenylboronic acid (0.31 g, 1.2 mmol) according to the general procedure III. Obtained as light yellow solid (0.06 g), which was subsequently deprotected.

2) To a cooled and stirred solution of 3-{1-[4-difluoromethyl-6-(6-trifluoromethyl-pyridin-3-yl)-pyrimidin-2-yl]-1H-imidazol-4-yl}-benzenesulfonic acid tert-butylamide (0.06 g) in dichloromethane (2 ml) was added TFA (2 ml) and the reaction mixture was allowed to stir at room temperature for 15 h. The mixture was evaporated to dryness, poured into 2N Na$_2$CO$_3$ solution (25 ml) and extracted with ethyl acetate (3×50 ml). The combined organic layers were washed with brine (50 ml), dried (MgSO$_4$) and evaporated. Further purification by column chromatography on silica gel (dichloromethane/MeOH/NH$_4$OH 16:1:0.1) and crystallization (diethyl ether) yielded the title compound as a white solid (0.022 g, 4%). MS (ISP) 497.2 [(M+H)$^+$]; mp 219.5° C.

Example 20

5-{1-[4-Methyl-6-(6-trifluoromethyl-pyridin-3-yl)-pyrimidin-2-yl]-1H-imidazol-4-yl}-pyridin-2-ylamine The title compound was prepared from 2-(4-iodo-imidazol-1-yl)-4-methyl-6-(6-trifluoromethyl-pyridin-3-yl)-pyrimidine (example B.9) (0.35 g, 0.81 mmol) and commercially available 2-amino-5-(4,4,5,5-tetramethyl-1,3,2-dioxaborolan-2-yl)pyridine (0.214 g, 0.97 mmol) according to the general procedure III. Obtained as a yellow solid (0.19 g, 59%). MS (ISP) 398.2 [(M+H)$^+$]; mp 220° C.

Example 21

3-{4-[4-Methyl-6-(6-trifluoromethyl-pyridin-3-yl)-pyrimidin-2-yl]-pyridin-2-yl}-benzenesulfonamide 1) 3-{4-[4-Methyl-6-(6-trifluoromethyl-pyridin-3-yl)-pyrimidin-2-yl]-pyridin-2-yl}-benzenesulfonic acid tert-butylamide was prepared from 2-(2-chloro-pyridin-4-yl)-4-methyl-6-(6-trifluoromethyl-pyridin-3-yl)-pyrimidine (example B.10) (0.175 g, 0.5 mmol) and commercially available 3-(tert.-butylsulfamoyl)-phenylboronic acid (0.15 g, 0.6 mmol) according to the general procedure III. Obtained as off-white solid (0.08 g), which was subsequently deprotected.

2) To a cooled and stirred solution of 3-{4-[4-methyl-6-(6-trifluoromethyl-pyridin-3-yl)-pyrimidin-2-yl]-pyridin-2-yl}-benzenesulfonic acid tert-butylamide (0.08 g) in dichloromethane (2 ml) was added TFA (2 ml) and the reaction mixture was allowed to stir at room temperature for 15 h. The mixture was evaporated to dryness, poured into 2N Na$_2$CO$_3$ solution (20 ml) and extracted with ethyl acetate (3×50 ml). The combined organic layers were washed with brine (50 ml), dried (MgSO$_4$) and evaporated. Further purification by crystallization (ethyl acetate/heptane) yielded the title compound as a white solid (0.036 g, 15%). MS (ISP) 472.2 [(M+H))$^+$]; mp 255° C.

Example 22

5-{4-[4-Methyl-6-(6-trifluoromethyl-pyridin-3-yl)-pyrimidin-2-yl]-pyridin-2-yl}-thiophene-2-sulfonic acid amide 1) 5-{4-[4-Difluoromethyl-6-(6-methyl-pyridin-3-yl)-pyrimidin-2-yl]-pyridin-2-yl}-thiophene-2-sulfonic-acid tert-butylamide was prepared from 2-(2-chloro-pyridin-4-yl)-4-methyl-6-(6-trifluoromethyl-pyridin-3-yl)-pyrimidine (example B.10) (0.175 g, 0.5 mmol) and N-tert-butyl-5-(4,4,5,5-tetramethyl-1,3,2-dioxaborolan-2-yl)-thiophene-2-sulfonamide (example C.1) (0.21 g, 0.6 mmol) according to the general procedure III. Obtained as an off-white solid (0.11 g), which was subsequently deprotected.

2) To a cooled and stirred solution of 5-{4-[4-methyl-6-(6-trifluoromethyl-pyridin-3-yl)-pyrimidin-2-yl]-pyridin-2-yl}-thiophene-2-sulfonic-acid tert-butylamide (0.11 g) in dichloromethane (3 ml) was added TFA (3 ml) and the reaction mixture was allowed to stir at room temperature for 15 h. The mixture was evaporated to dryness, poured into 2N Na$_2$CO$_3$ solution (20 ml) and extracted with ethyl acetate (3×50 ml). The combined organic layers were washed with brine (50 ml), dried (MgSO$_4$) and evaporated. Further purification by column chromatography on silica gel (dichloromethane/MeOH/NH$_4$OH 16:1:0.1) and crystallization (MeOH, diethyl ether) yielded the title compound as a white solid (0.016 g, 7%). MS (ISP) 478.1 [(M+H)$^+$]; mp 289° C.

Example 23

3'-[4-Methyl-6-(6-trifluoromethyl-pyridin-3-yl)-pyrimidin-2-yl]-biphenyl-3-sulfonic acid amide 1) 3'-[4-Methyl-6-(6-trifluoromethyl-pyridin-3-yl)-pyrimidin-2-yl]-biphenyl-3-sulfonic acid tert-butylamide was prepared from 2-(3-bromo-phenyl)-4-methyl-6-(6-trifluoromethyl-pyridin-3-yl)-pyrimidine (example B.11) (0.197 g, 0.5 mmol) and commercially available 3-(tert.-butylsulfamoyl)-phenylboronic acid (0.15 g, 0.6 mmol) according to the general procedure III. Obtained as light yellow solid (0.24 g), which was subsequently deprotected.

2) To a cooled and stirred solution of 3'-[4-methyl-6-(6-trifluoromethyl-pyridin-3-yl)-pyrimidin-2-yl]-biphenyl-3-sulfonic acid tert-butylamide (0.24 g) in dichloromethane (6 ml) was added TFA (6 ml) and the reaction mixture was allowed to stir at room temperature for 15 h. The mixture was evaporated to dryness, poured into 2N $Na_2CO_3$ solution (25 ml) and extracted with ethyl acetate (3×50 ml). The combined organic layers were washed with brine (50 ml), dried ($MgSO_4$) and evaporated. Further purification by crystallization (ethyl acetate/heptane) yielded the title compound as a white solid (0.081 g, 34%). MS (ISP) 471.2 [(M+H)$^+$]; mp 220° C.

Example 24

5-{3-[4-Methyl-6-(6-trifluoromethyl-pyridin-3-yl)-pyrimidin-2-yl]-phenyl}-thiophene-2-sulfonic acid amide 1) N-tert-Butyl-5-{3-[4-methyl-6-(6-trifluoromethyl-pyridin-3-yl)-pyrimidin-2-yl]-phenyl}-thiophene-2-sulfonic acid amide was prepared from 2-(3-bromo-phenyl)-4-methyl-6-(6-trifluoromethyl-pyridin-3-yl)-pyrimidine (example B.11) (0.197 g, 0.5 mmol) and N-tert-butyl-5-(4,4,5,5-tetramethyl-1,3,2-dioxaborolan-2-yl)-thiophene-2-sulfonamide (example C.1) (0.21 g, 0.6 mmol) according to the general procedure III. Obtained as an off-white solid (0.1 g), which was subsequently deprotected.

2) To a cooled and stirred solution of N-tert-butyl-5-{3-[4-methyl-6-(6-trifluoromethyl-pyridin-3-yl)-pyrimidin-2-yl]-phenyl}-thiophene-2-sulfonic acid amide (0.1 g) in dichloromethane (4 ml) was added TFA (4 ml) and the reaction mixture was allowed to stir at room temperature for 15 h. The mixture was evaporated to dryness, poured into 2N $Na_2CO_3$ solution (25 ml) and extracted with ethyl acetate (3×50 ml). The combined organic layers were washed with brine (50 ml), dried ($MgSO_4$) and evaporated. Further purification by column chromatography on silica gel (dichloromethane/MeOH/$NH_4OH$ 16:1:0.1) and crystallization (diethyl ether/MeOH) yielded the title compound as a white solid (6 mg, 3%). MS (ISP) 477.1 [(M+H)$^+$]; mp 237.5° C.

Example 25

N-tert-Butyl-3-{6-[4-methyl-6-(6-trifluoromethyl-pyridin-3-yl)-pyrimidin-2-yl]-pyridin-2-yl}-benzenesulfonamide Prepared According to the General Procedure IV:

3-Aryl-2-alkyne-1-one part 1) 4-(5-Trifluoromethyl-pyridin-2-yl)-but-3-yn-2-ol: Commercially available 5-bromo-2-(trifluoromethyl)pyridine [CAS-no. 436799-32-5] (1.0 g, 4.44 mmol), commercially available 3-butyn-2-ol [CAS-no. 2028-63-9] (0.49 ml, 6.66 mmol), triethylamine (1.23 ml, 8.88 mmol), Pd(PPh$_3$)$_2$Cl$_2$ (31 mg, 1 mol %) and triphenylphosphine (23 mg, 2 mol %) were dissolved in THF (15 ml), argon was bubbled through the suspension for 20 minutes, then copper (I) iodide (8 mg, 1 mol %) was added and the mixture was stirred at 80° C. for 12 h. The reaction mixture was poured onto water, then extracted three times with ethyl acetate, the combined organic layers were dried over MgSO$_4$, filtered and the solvents evaporated to give the crude product (4 g) as a brown liquid, which was purified by flash chromatography with n-heptane and ethyl acetate to give the 4-(5-trifluoromethyl-pyridin-2-yl)-but-3-yn-2-ol as a brown liquid (0.915 g, 96%). MS (ISP) 216.2 [(M+H)$^+$].

2) 4-(5-Trifluoromethyl-pyridin-2-yl)-but-3-yn-2-one: The above described 4-(5-trifluoromethyl-pyridin-2-yl)-but-3-yn-2-ol (0.885 g, 4.1 mmol) was dissolved in methylene chloride (20 ml), cooled to 0° C., then Dess-Martin periodinane (1.88 g, 4.32 mmol) was added and the mixture was stirred at 0° C. for 2 h. To the reaction mixture was added diethyl ether, the precipitate filtered off, washed with diethyl ether, the filtrate was extracted with diethyl ether and saturated NaHCO$_3$-sol., the organic layers were dried over MgSO$_4$, filtered and the solvents were evaporated to give the 4-(5-trifluoromethyl-pyridin-2-yl)-but-3-yn-2-one as a brown solid (0.888 g, 100%), which was used without further purification. MS (EI) 213.1 [M$^+$].

Amidine Part:

1) 3-(6-Bromo-pyridin-2-yl)-N-tert-butyl-benzenesulfonamide: A mixture of commercially available 3-(tert-butylsulfamoyl)-benzeneboronic acid [CAS-no. 221290-14-8] (5.142 g, 20 mmol), commercially available 2,6-dibromopyridine (14.2 g, 60 mmol) and Pd(PPh$_3$)$_4$ (1.156 g, 5 mol %) in DME (80 ml) and aqueous sodium carbonate (1 M, 40 ml, 40 mmol) was stirred at 90° C. under argon atmosphere for 18 h. The reaction mixture was extracted with water and ethyl acetate, the organic layers dried over MgSO$_4$, filtered and the solvents evaporated. The crude product was purified by flash chromatography with n-heptane/ethyl acetate to give the 3-(6-bromo-pyridin-2-yl)-N-tert-butyl-benzenesulfonamide (6.60 g, 89%) as a yellow solid. MS (ISP) 369.1 [(M+H)$^+$] and 371.0 [(M+2+H)$^+$].

2) N-tert-Butyl-3-(6-cyano-pyridin-2-yl)-benzenesulfonamide: A mixture of the above described 3-(6-bromo-pyridin-2-yl)-N-tert-butyl-benzenesulfonamide (3.12 g, 8 mmol) and copper(I) cyanide (1.6 g, 18 mmol) in NMP (15 ml) was stirred at 120° C. for 1 h. Cooled to rt, the reaction mixture was extracted with aqueous ammonia and ethyl acetate, the organic layers were dried over MgSO$_4$, filtered and the solvents were evaporated. The crude product was purified by flash chromatography with n-heptane and ethyl acetate to give the N-tert-butyl-3-(6-cyano-pyridin-2-yl)-benzenesulfonamide (1.05 g, 39%) as a light brown oil. MS (ISP) 316.1 [(M+H)$^+$].

3) 6-(3-tert-Butylsulfamoyl-phenyl)-N-hydroxy-pyridine-2-carboxamidine: A mixture of the above described N-tert-butyl-3-(6-cyano-pyridin-2-yl)-benzenesulfonamide (1.03 g, 3.27 mmol), hydroxylamine hydrochloride (794 mg, 11.4 mmol) and sodium carbonate (692 mg, 6.53 mmol) in EtOH (20 ml) and water (20 ml) was stirred under argon atmosphere at 100° C. for 2 h. The EtOH was evaporated, the mixture was diluted with water and stirred for 1 h at 0° C. The crude product was filtered and dried in HV to give the pure 6-(3-tert-butylsulfamoyl-phenyl)-N-hydroxy-pyridine-2-carboxamidine as a white solid (850 mg, 75%). MS (ISP) 349.3 [(M+H))$^+$].

4) 6-(3-tert-Butylsulfamoyl-phenyl)-pyridine-2-carboxamidinium acetate: To a mixture of the above described 6-(3-tert-butylsulfamoyl-phenyl)-N-hydroxy-pyridine-2-carboxamidine (Example C.7) (830 mg, 2.38 mmol) in acetic acid (10 ml) at 23° C. was added acetic anhydride (0.34 ml, 3.57 mmol) and the mixture was stirred at 23° C. for 10 min, then 10% Pd on charcoal (84 mg, 0.79 mmol) was added and the mixture was hydrogenated (1 bar hydrogen) at 23° C. for 24 h. The catalyst was filtered off, washed with acetic acid and the solvents were evaporated to give the 6-(3-tert-butylsulfamoyl-phenyl)-pyridine-2-carboxamidinium acetate (1.38 g, 148%, contains excess acetic acid) as a light yellow oil, which was used without further purification (cf Synth. Commun. 1996, 26(23), 4351). MS (ISP) 333.1 [(M+H)+].

Condensation reaction: The above described 4-(5-trifluoromethyl-pyridin-2-yl)-but-3-yn-2-one (53 mg, 0.25 mmol), the also above described 6-(3-tert-butylsulfamoyl-phenyl)-pyridine-2-carboxamidinium acetate (118 mg, 0.3 mmol) and sodium carbonate (64 mg, 0.6 mmol) were dissolved in acetonitrile (2 ml) and treated by microwave irradiation at 120° C. for 60 min. The reaction mixture was extracted with ethyl acetate and water, the organic layers were combined, dried over MgSO$_4$, filtered and the solvents were evaporated to give a crude product, which was purified by flash chromatography with n-heptane and ethyl acetate to give the title compound as a light brown foam (63 mg, 48%). MS (ISP) 528.2 [(M+H)+].

Example 26

N-tert-Butyl-3-{6-[4-methyl-6-(6-trifluoromethyl-pyridin-3-yl)-pyrimidin-2-yl]-pyridin-2-yl}-benzenesulfonamide Prepared According to the General Procedure IV:

3-Aryl-2-alkyne-1-one part 1) 4-(6-Trifluoromethyl-pyridin-3-yl)-but-3-yn-2-ol: Commercially available 2-bromo-5-(trifluoromethyl)pyridine [CAS-no. 50488-42-1] (3.33 g, 14.7 mmol), commercially available 3-butyn-2-ol [CAS-no. 2028-63-9] (1.63 ml, 22.2 mmol), triethylamine (6.2 ml, 29.5 mmol), Pd(PPh$_3$)$_2$Cl$_2$ (104 mg, 1 mol %) and triphenylphosphine (77 mg, 2 mol %) were dissolved in THF (50 ml), argon was bubbled through the suspension for 20 minutes, then copper (I) iodide (28 mg, 1 mol %) was added and the mixture was stirred at 80° C. for 12 h. The reaction mixture was poured onto water, then extracted three times with ethyl acetate, the combined organic layers were dried over MgSO$_4$, filtered and the solvents evaporated to give the crude product (4 g) as a brown liquid, which was purified by flash chromatography with n-heptane and ethyl acetate to give the 4-(6-trifluoromethyl-pyridin-3-yl)-but-3-yn-2-ol as a brown liquid (1.60 g, 50%). MS (ISP) 216.3 [(M+H)+].

2) 4-(6-Trifluoromethyl-pyridin-3-yl)-but-3-yn-2-one: The above prepared 4-(6-trifluoromethyl-pyridin-3-yl)-but-3-yn-2-ol (1.60 g, 7 mmol) was dissolved in methylene chloride (40 ml), cooled to 0° C., then Dess-Martin periodinane (3.41 g, 8 mmol) was added and the mixture was stirred at 0° C. for 2 h. To the reaction mixture was added diethyl ether, the precipitate filtered off, washed with diethyl ether, the filtrate was extracted with diethyl ether and saturated NaHCO$_3$-sol., the organic layers were dried over MgSO$_4$, filtered and the solvents were evaporated to give the 4-(6-trifluoromethyl-pyridin-3-yl)-but-3-yn-2-one as a brown solid (1.59 g, 100%), which was used without further purification. MS (EI) 213.1 [M+].

Condensation reaction: The above described 4-(6-trifluoromethyl-pyridin-3-yl)-but-3-yn-2-one (53 mg, 0.25 mmol), 6-(3-tert-butylsulfamoyl-phenyl)-pyridine-2-carboxamidinium acetate (Example 26, amidine part, steps 1 to 4) (118 mg, 0.3 mmol) and sodium carbonate (64 mg, 0.6 mmol) were dissolved in acetonitrile (2 ml) and treated by microwave irradiation at 120° C. for 60 min. The reaction mixture was extracted with ethyl acetate and water, the organic layers were combined, dried over MgSO$_4$, filtered and the solvents were evaporated to give a crude product, which was purified by flash chromatography with n-heptane and ethyl acetate to give the title compound as a light brown foam (100 mg, 76%). MS (ISP) 528.2 [(M+H)+].

Example 27

3-{6-[4-Methyl-6-(5-trifluoromethyl-pyridin-2-yl)-pyrimidin-2-yl]-pyridin-2-yl}-benzenesulfonamide To N-tert-butyl-3-{6-[4-methyl-6-(6-trifluoromethyl-pyridin-3-yl)-pyrimidin-2-yl]-pyridin-2-yl}-benzenesulfonamide (Example 25) (0.056 g, 0.106 mmol) was added TFA (2 mL) and the reaction mixture was stirred at 23° C. for 16 h. The mixture was partitioned between EtOAc and saturated NaHCO$_3$ solution, the organic layer was dried over Na$_2$SO$_4$. Removal of the solvent in vacuum left a crude product which was triturated with diethyl ether to give the title compound as an off-white solid (0.050 g, 100%). MS (ISP) 471.9 [(M+H)+]; mp 246-252° C.

Example 28

3-{6-[4-Methyl-6-(6-trifluoromethyl-pyridin-3-yl)-pyrimidin-2-yl]-pyridin-2-yl}-benzenesulfonamide To N-tert-butyl-3-{6-[4-methyl-6-(6-trifluoromethyl-pyridin-3-yl)-pyrimidin-2-yl]-pyridin-2-yl}-benzenesulfonamide (Example 26) (0.092 g, 0.174 mmol) was added TFA (2 mL) and the reaction mixture was stirred at 23° C. for 16 h. The mixture was partitioned between EtOAc and saturated NaHCO$_3$ solution, the organic layer was dried over Na$_2$SO$_4$. Removal of the solvent in vacuum left a crude product which was triturated with diethyl ether to give the title compound as an off-white solid (0.080 g, 98%). MS (ISP) 472.0 [(M+H)+]; mp 254° C.

Example 29

N-tert-Butyl-3-(6'-methyl-6"-trifluoromethyl-[2,2';4',3"]terpyridin-6-yl)-benzenesulfonamide A stirred mixture of trifluoro-methanesulfonic acid 6'-methyl-6-trifluoromethyl-[3,4']bipyridinyl-2'-yl ester (Example A.5) (0.193 g, 0.5 mmol), N-tert-butyl-3-(6-tributylstannanyl-pyridin-2-yl)-benzenesulfonamide (Example C.2) (0.264 g, 0.455 mmol), tetrakis(triphenyl-phosphine)palladium (0.029 g, 5 mol %) in toluene (5 mL) was heated under reflux conditions for 18 h. Cooled to rt, extracted with ethyl acetate and water, dried the organic layer over Na$_2$SO$_4$. Removal of the solvent in vacuum left a crude product which was purified by silica gel column chromatography with n-heptane/ethyl acetate to give the title compound after trituration with diethyl ether as a white solid (110 mg, 42%). MS (ISP) 527.0 [(M+H)+]; mp 187-188° C.

Example 30

3-(6'-Methyl-6"-trifluoromethyl-[2,2';4',3"]terpyridin-6-yl)-benzenesulfonamide

To N-tert-butyl-3-(6'-methyl-6"-trifluoromethyl-[2,2';4',3"]terpyridin-6-yl)-benzenesulfonamide (Example 29) (0.075 g, 0.142 mmol) was added TFA (2 mL) and the reaction mixture was stirred at 23° C. for 16 h. The mixture was partitioned between EtOAc and saturated NaHCO₃ solution, the organic layer was dried over Na₂SO₄. Removal of the solvent in vacuum left a crude product which was triturated with diethyl ether to give the title compound as an off-white solid (0.032 g, 48%). MS (ISP) 471.0 [(M+H)⁺]; mp 233-234° C.

Example 31

3'-(6'-Methyl-6-trifluoromethyl-[3,4']bipyridinyl-2'-yl)-biphenyl-3-sulfonic acid tert-butylamide The title compound was prepared from 6'-(3-bromo-phenyl)-2'-methyl-6-trifluoromethyl-[3,4']bipyridinyl (example B.12) (0.197 g, 0.5 mmol) and commercially available 3-(tert-butylsulfamoyl)-benzeneboronic acid (0.142 g, 0.55 mmol) according to the general procedure III. Obtained as a white foam (0.245 g, 93%). MS (ISP) 526.7 [(M+H)⁺].

Example 32

5-[3-(6'-Methyl-6-trifluoromethyl-[3,4']bipyridinyl-2'-yl)-phenyl]-pyridin-2-ylamine The title compound was prepared from 6'-(3-bromo-phenyl)-2'-methyl-6-trifluoromethyl-[3,4']bipyridinyl (example B.12) (0.197 g, 0.5 mmol) and N-tert-butyl-5-(4,4,5,5-tetramethyl-1,3,2-dioxaborolan-2-yl)-thiophene-2-sulfonamide (example C.1) (0.190 g, 0.55 mmol) according to the general procedure III. Obtained as a white foam (0.130 g, 49%). MS (ISP) 532.6 [(M+H)⁺].

Example 33

5-[3-(6'-Methyl-6-trifluoromethyl-[3,4']bipyridinyl-2'-yl)-phenyl]-pyridin-2-ylamine The title compound was prepared from 6'-(3-bromo-phenyl)-2'-methyl-6-trifluoromethyl-[3,4']bipyridinyl (example B.12) (0.098 g, 0.25 mmol) and commercially available 2-amino-5-(4,4,5,5-tetramethyl-1,3,2-dioxaborolan-2-yl) pyridine (0.61 g, 0.275 mmol) according to the general procedure III. Obtained as an off-white solid (0.031 g, 31%). MS (ISP) 407.3 [(M+H)⁺]; mp 124-125° C.

Example 34

3'-(6'-Methyl-6-trifluoromethyl-[3,4']bipyridinyl-2'-yl)-biphenyl-3-sulfonic acid amide To 3'-(6'-methyl-6-trifluoromethyl-[3,4']bipyridinyl-2'-yl)-biphenyl-3-sulfonic acid tert-butylamide (Example 31) (0.150 g, 0.285 mmol) was added TFA (2 mL) and the reaction mixture was stirred at 23° C. for 16 h. The mixture was partitioned between EtOAc and saturated NaHCO₃ solution, the organic layer was dried over Na₂SO₄. Removal of the solvent in vacuum left a crude product which was triturated with diethyl ether to give the title compound as a white solid (0.090 g, 75%). MS (ISP) 470.1 [(M+H)⁺]; mp 227-232° C.

Example 35

5-[3-(6'-Methyl-6-trifluoromethyl-[3,4']bipyridinyl-2'-yl)-phenyl]-thiophene-2-sulfonic acid amide To 5-[3-(6'-methyl-6-trifluoromethyl-[3,4']bipyridinyl-2'-yl)-phenyl]-pyridin-2-ylamine (Example 32) (0.100 g, 0.188 mmol) was added TFA (2 mL) and the reaction mixture was stirred at 23° C. for 16 h. The mixture was partitioned between EtOAc and saturated NaHCO₃ solution, the organic layer was dried over Na₂SO₄. Removal of the solvent in vacuum left a crude product which was triturated with diethyl ether to give the title compound as a white solid (0.090 g, 100%). MS (ISP) 476.8 [(M+H)⁺]; mp 231-233° C.

The invention claimed is:
1. A compound of formula (I):

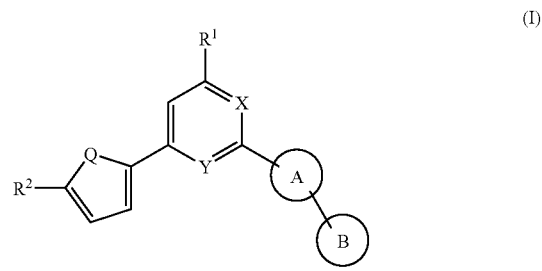

wherein
X and Y are N;
Q is S, O, —CH═N— or —N═CH—;
A is aryl or 5 or 6 membered heteroaryl each of which is optionally substituted by $C_{1-6}$-alkyl;
B is an optionally substituted 5 or 6 membered heteroaryl, wherein the substituents are selected from the group consisting of:
halo,
nitro,
$C_{1-6}$-alkyl optionally substituted by hydroxy,
$NR^aR^b$, wherein $R^a$ and $R^b$ are independently H, $C_{1-6}$-alkyl or —(CO)—$C_{1-6}$-alkyl,
—S—$C_{1-6}$-alkyl,
—(SO₂)—OH,
—(SO₂)—$C_{1-6}$-alkyl,
—(SO₂)—$NR^cR^d$, wherein $R^c$ and $R^d$ are independently:
H,
$C_{1-6}$-alkyl optionally substituted by hydroxy,
$C_{1-6}$-haloalkyl,
$C_{1-6}$-alkoxy,
—(CO)$C_{1-6}$-alkyl optionally substituted by $C_{1-6}$-alkoxy,
—(CH₂CH₂O)ₙCHR^e, wherein $R^e$ is H or CH₂OH and n is 1, 2, 3, 4, 5, 6, 7, 8, 9 or 10,
—(CH₂)ₘ-aryl, wherein m is 1 or 2 and the aryl is optionally substituted by halo or $C_{1-6}$-alkoxy,
—(CH₂)ₚ—$C_{3-6}$-cycloalkyl, wherein p is 0 or 1, or
5 or 6-membered heterocycloalkyl,
—(SO₂)—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an SO₂ group, wherein said 4, 5 or 6 membered heterocycloalkyl ring is optionally substituted by a substituent selected from the group consisting of:
hydroxy, $C_{1-6}$-alkyl, $C_{1-6}$-alkoxy which is optionally substituted by
hydroxy, and 5 or 6 membered heteroaryloxy,
NHSO₂—$C_{1-6}$-alkyl, and
NHSO₂—$NR^hR^i$ wherein $R^h$ and $R^i$ are independently H, $C_{1-6}$-alkyl, —(CO)O—$C_{1-6}$-alkyl, or $R^h$ and $R^i$ together with the nitrogen atom to which they are attached form a 4, 5 or 6 membered heterocycloalkyl ring optionally containing a further heteroatom selected from nitrogen, oxygen and sulphur, wherein said 4, 5 or 6 membered heterocycloalkyl ring is optionally substituted by $C_{1-6}$-alkyl, $R^1$ is H, halogen, $C_{1-6}$-alkyl optionally substituted by hydroxy, $C_{1-6}$-alkoxy, $C_{1-6}$-haloalkyl, or $C_{3-6}$-cycloalkyl; and $R^2$ is selected from the group consisting of cyano, halogen, $C_{1-6}$-haloalkyl, $C_{1-6}$-alkoxy, $C_{1-6}$-haloalkoxy, $C_{1-6}$-alkyl and $C_{3-6}$-cycloalkyl;

or is $NR^jR^k$ wherein $R^j$ and $R^k$ are each independently selected from the group consisting of H, $C_{3-8}$-cycloalkyl, aryl, heteroaryl having from 5 to 12 ring atoms and $C_{1-6}$-alkyl which optionally substituted by one or more substituent(s) selected from the group consisting of halogen, hydroxy, $C_{3-8}$-cycloalkyl, aryl, heteroaryl having from 5 to 12 ring atoms and —$NR^lR^m$, wherein $R^l$ and $R^m$ are independently selected from the group consisting of H and $C_{1-6}$-alkyl;

or $R^l$ and $R^m$ can, together with the nitrogen atom to which they are attached, form an optionally substituted heterocyclic group comprising 5 to 12 ring atoms optionally containing a further heteroatom selected from nitrogen, oxygen or sulphur, wherein said heterocyclic group is optionally substituted by one, two, three, four or five substituents are selected from the group consisting of halogen, hydroxy, $C_{1-6}$-alkyl and $C_{1-6}$-haloalkyl;

or a pharmaceutically acceptable salt thereof.

2. The compound of claim 1, wherein:
X and Y are N;
Q is S, —CH═N—, or —N═CH—;
A is aryl or 5 or 6 membered heteroaryl;
B is an optionally substituted 5 or 6 membered heteroaryl, wherein the substituents are selected from the group consisting of
$NR^aR^b$, wherein $R^a$ and $R^b$ are independently H, and —$(SO_2)$—$NR^cR^d$, wherein $R^c$ and $R^d$ are independently:
H,
$C_{1-6}$-alkyl, or
—(CO)$C_{1-6}$-alkyl;
$R^1$ is $C_{1-6}$-alkyl or $C_{1-6}$-haloalkyl; and
$R^2$ is 5 or 6 membered heteroaryl optionally substituted by one, two or three substituents selected from the group consisting of halogen and $C_{1-6}$-haloalkyl;
or a pharmaceutically acceptable salt thereof.

3. A compound of formula (Ia):

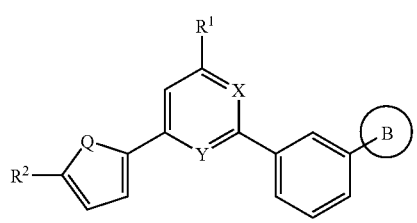

(Ia)

wherein
X and Y are N;
Q is S, O, —CH═N— or —N═CH—;

B is an optionally substituted aryl or an optionally substituted 5 or 6 membered heteroaryl, wherein the substituents are selected from the group consisting of:
halo,
nitro,
$C_{1-6}$-alkyl optionally substituted by hydroxy,
$NR^aR^b$, wherein $R^a$ and $R^b$ are independently H, $C_{1-6}$-alkyl or —(CO)—$C_{1-6}$-alkyl,
—S—$C_{1-6}$-alkyl,
—$(SO_2)$—OH,
—$(SO_2)$—$C_{1-6}$-alkyl,
—$(SO_2)$—$NR^cR^d$, wherein $R^c$ and $R^d$ are independently:
H,
$C_{1-6}$-alkyl optionally substituted by hydroxy,
$C_{1-6}$-haloalkyl,
$C_{1-6}$-alkoxy,
—(CO)$C_{1-6}$-alkyl optionally substituted by $C_{1-6}$-alkoxy,
—$(CH_2CH_2O)_nCHR^e$, wherein $R^e$ is H or $CH_2OH$ and n is 1, 2, 3, 4, 5, 6, 7, 8, 9 or 10,
—$(CH_2)_m$-aryl, wherein m is 1 or 2 and the aryl is optionally substituted by halo or $C_{1-6}$-alkoxy,
—$(CH_2)_p$—$C_{3-6}$-cycloalkyl, wherein p is 0 or 1, 5 or 6-membered heterocycloalkyl,
—$(SO_2)$—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of:
hydroxy, $C_{1-6}$-alkyl, $C_{1-6}$-alkoxy which is optionally substituted by
hydroxy, and 5 or 6 membered heteroaryloxy,
$NHSO_2$—$C_{1-6}$-alkyl, and
$NHSO_2$—$NR^hR^i$ wherein $R^h$ and $R^i$ are independently H, $C_{1-6}$-alkyl, —(CO)O—$C_{1-6}$-alkyl, or $R^h$ and $R^i$ together with the nitrogen atom to which they are attached form a 4, 5 or 6 membered heterocycloalkyl ring optionally containing a further heteroatom selected from nitrogen, oxygen and sulphur, wherein said 4, 5 or 6 membered heterocycloalkyl ring is optionally substituted by $C_{1-6}$-alkyl, $R^1$ is H, halogen, $C_{1-6}$-alkyl optionally substituted by hydroxy, $C_{1-6}$-alkoxy, $C_{1-6}$-haloalkyl, or $C_{3-6}$-cycloalkyl; and $R^2$ is selected from the group consisting of cyano, halogen, $C_{1-6}$-haloalkyl, $C_{1-6}$-alkoxy, $C_{1-6}$-haloalkoxy, $C_{1-6}$-alkyl and $C_{3-6}$-cycloalkyl;

or is $NR^jR^k$ wherein $R^j$ and $R^k$ are each independently selected from the group consisting of H, $C_{3-8}$-cycloalkyl, aryl, heteroaryl having from 5 to 12 ring atoms and $C_{1-6}$-alkyl which optionally substituted by one or more substituent(s) selected from the group consisting of halogen, hydroxy, $C_{3-8}$-cycloalkyl, aryl, heteroaryl having from 5 to 12 ring atoms and —$NR^lR^m$, wherein $R^l$ and $R^m$ are independently selected from the group consisting of H and $C_{1-6}$-alkyl;

or $R^l$ and $R^m$ can, together with the nitrogen atom to which they are attached, form an optionally substituted heterocyclic group comprising 5 to 12 ring atoms optionally containing a further heteroatom selected from nitrogen, oxygen and sulphur, wherein said heterocyclic group is optionally substituted by one, two, three, four or five substituents are selected from the group consisting of halogen, hydroxy, C$_{1-6}$-alkyl and C$_{1-6}$-haloalkyl;

or a pharmaceutically acceptable salt thereof.

4. The compound of claim 3, wherein B is an optionally substituted aryl or an optionally substituted 5 or 6 membered heteroaryl, wherein the substituent is NR$^a$R$^b$, and wherein R$^a$ and R$^b$ are both H.

5. The compound of claim 4, selected from the group consisting of
   5-{3-[4-(5-Chloro-thiophen-2-yl)-6-trifluoromethyl-pyrimidin-2-yl]-phenyl}-pyridin-2-ylamine;
   5-{3-[4-(5-Chloro-thiophen-2-yl)-6-trifluoromethyl-pyrimidin-2-yl]-phenyl}-pyrimidin-2-ylamine; and
   5-{3-[4-Trifluoromethyl-6-(6-trifluoromethyl-pyridin-3-yl)-pyrimidin-2-yl]-phenyl}-pyridin-2-ylamine.

6. The compound of claim 3, wherein B is an optionally substituted aryl or an optionally substituted 5 or 6 membered heteroaryl, wherein the substituent is NR$^a$R$^b$, wherein R$^a$ and R$^b$ are H and —(SO$_2$)—NR$^c$R$^d$, wherein R$^c$ and R$^d$ are independently H, C$_{1-6}$-alkyl, or —(CO)C$_{1-6}$-alkyl.

7. The compound of claim 6, selected from the group consisting of
   3'-[4-Trifluoromethyl-6-(6-trifluoromethyl-pyridin-3-yl)-pyrimidin-2-yl]-biphenyl-3-sulfonic acid amide;
   5-{3-[4-Trifluoromethyl-6-(6-trifluoromethyl-pyridin-3-yl)-pyrimidin-2-yl]-phenyl}-thiophene-2-sulfonic acid amide;
   3'-[4-(5-Chloro-thiophen-2-yl)-6-trifluoromethyl-pyrimidin-2-yl]-biphenyl-3-sulfonic acid amide;
   5-{3-[4-(5-Chloro-thiophen-2-yl)-6-trifluoromethyl-pyrimidin-2-yl]-phenyl}-thiophene-2-sulfonic acid amide;
   3'-[4-Difluoromethyl-6-(6-trifluoromethyl-pyridin-3-yl)-pyrimidin-2-yl]-biphenyl-3-sulfonic acid amide;
   5-{3-[4-Difluoromethyl-6-(6-trifluoromethyl-pyridin-3-yl)-pyrimidin-2-yl]-phenyl}-thiophene-2-sulfonic acid amide;
   3'-[4-Methyl-6-(6-trifluoromethyl-pyridin-3-yl)-pyrimidin-2-yl]-biphenyl-3-sulfonic acid amide; and
   5-{3-[4-Methyl-6-(6-trifluoromethyl-pyridin-3-yl)-pyrimidin-2-yl]-phenyl}-thiophene-2-sulfonic acid amide.

8. A compound of formula (Ib):

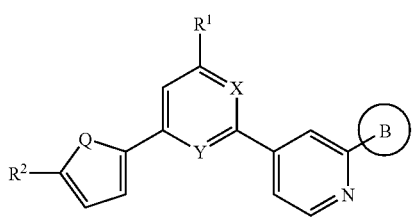

(Ib)

wherein
X and Y are N;
Q is S, O, —CH=N— or —N=CH—;
B is an optionally substituted aryl or an optionally substituted 5 or 6 membered heteroaryl, wherein the substituents are selected from the group consisting of:
   halo,
   nitro,
   C$_{1-6}$-alkyl optionally substituted by hydroxy,
   NR$^a$R$^b$, wherein R$^a$ and R$^b$ are independently H, C$_{1-6}$-alkyl or —(CO)—C$_{1-6}$-alkyl,
   —S—C$_{1-6}$-alkyl,
   —(SO$_2$)—OH,
   —(SO$_2$)—C$_{1-6}$-alkyl,
   —(SO$_2$)—NR$^c$R$^d$, wherein R$^c$ and R$^d$ are independently:
      H,
      C$_{1-6}$-alkyl optionally substituted by hydroxy,
      C$_{1-6}$-haloalkyl,
      C$_{1-6}$-alkoxy,
      —(CO)C$_{1-6}$-alkyl optionally substituted by C$_{1-6}$-alkoxy, —(CH$_2$CH$_2$O)$_n$CHR$^e$, wherein R$^e$ is H or CH$_2$OH and n is 1, 2, 3, 4, 5, 6, 7, 8, 9 or 10,
      —(CH$_2$)$_m$-aryl, wherein m is 1 or 2 and the aryl is optionally substituted by halo or C$_{1-6}$-alkoxy,
      —(CH$_2$)$_p$—C$_{3-6}$-cycloalkyl, wherein p is 0 or 1, 5 or 6-membered heterocycloalkyl,
   —(SO$_2$)—NR$^f$R$^g$, wherein R$^f$ and R$^g$ together with the nitrogen atom to which they are attached form a 4, 5 or 6 membered heterocycloalkyl ring optionally containing a further heteroatom selected from nitrogen, oxygen, sulphur and an SO$_2$ group, wherein said 4, 5 or 6 membered heterocycloalkyl ring is optionally substituted by a substituent selected from the group consisting of
      hydroxy, C$_{1-6}$-alkoxy which is optionally substituted by
      hydroxy, and 5 or 6 membered heteroaryloxy,
   NHSO$_2$—C$_{1-6}$-alkyl, and
   NHSO$_2$—NR$^h$R$^i$ wherein R$^h$ and R$^i$ are independently H, —(CO)O—C$_{1-6}$-alkyl, or R$^h$ and R$^i$ together with the nitrogen atom to which they are attached form a 4, 5 or 6 membered heterocycloalkyl ring optionally containing a further heteroatom selected from nitrogen, oxygen or sulphur, wherein said 4, 5 or 6 membered heterocycloalkyl ring is optionally substituted by C$_{1-6}$-alkyl, R$^1$ is H, halogen, C$_{1-6}$-alkyl optionally substituted by hydroxy, C$_{1-6}$-alkoxy, C$_{1-6}$-haloalkyl, or C$_{3-6}$-cycloalkyl; and R$^2$ is selected from the group consisting of cyano, halogen, C$_{1-6}$-haloalkyl, O$_{1-6}$-alkoxy, C$_{1-6}$-haloalkoxy, C$_{1-6}$-alkyl and C$_{3-6}$-cycloalkyl;
   or is NR$^j$R$^k$ wherein R$^j$ and R$^k$ are each independently selected from the group consisting of
      H, C$_{3-8}$-cycloalkyl, aryl, heteroaryl having from 5 to 12 ring atoms and C$_{1-6}$-alkyl which optionally substituted by one or more substituent(s) selected from the group consisting of halogen, hydroxy, C$_{3-8}$-cycloalkyl, aryl, heteroaryl having from 5 to 12 ring atoms and —NR$^l$R$^m$, wherein R$^l$ and R$^m$ are independently selected from the group consisting of H and C$_{1-6}$-alkyl;
   or R$^l$ and R$^m$ can, together with the nitrogen atom to which they are attached, form an optionally substituted heterocyclic group comprising 5 to 12 ring atoms optionally containing a further heteroatom selected from nitrogen, oxygen or sulphur, wherein said heterocyclic group is optionally substituted by one, two, three, four or five substituents are selected from the group consisting of halogen, hydroxy, C$_{1-6}$-alkyl and C$_{1-6}$-haloalkyl;

or a pharmaceutically acceptable salt thereof.

9. The compound of claim 8, wherein B is an optionally substituted aryl or an optionally substituted 5 or 6 membered heteroaryl, wherein the substituent is NR$^a$R$^b$, wherein R$^a$ and R$^b$ are both H.

10. The compound of claim 9, which is 4-[4-Trifluoromethyl-6-(6-trifluoromethyl-pyridin-3-yl)-pyrimidin-2-yl]-[2,3']bipyridinyl-6'-ylamine.

11. The compound of claim 8, wherein B is an optionally substituted aryl or an optionally substituted 5 or 6 membered heteroaryl, wherein the substituent is $NR^aR^b$, wherein $R^a$ and $R^b$ are H and $-(SO_2)-NR^cR^d$, wherein $R^c$ and $R^d$ are independently H, $C_{1-6}$-alkyl, or $-(CO)C_{1-6}$-alkyl.

12. The compound of claim 11, selected from the group consisting of:
   3-{4-[4-Trifluoromethyl-6-(6-trifluoromethyl-pyridin-3-yl)-pyrimidin-2-yl]-pyridin-2-yl}-benzenesulfonamide;
   5-{4-[4-Trifluoromethyl-6-(6-trifluoromethyl-pyridin-3-yl)-pyrimidin-2-yl]-pyridin-2-yl}-thiophene-2-sulfonic acid amide;
   N-Propionyl-3-{4-[4-trifluoromethyl-6-(6-trifluoromethyl-pyridin-3-yl)-pyrimidin-2-yl]-pyridin-2-yl}-benzenesulfonamide;
   3-{4-[4-Difluoromethyl-6-(6-trifluoromethyl-pyridin-3-yl)-pyrimidin-2-yl]-pyridin-2-yl}-benzenesulfonamide;
   5-{4-[4-Difluoromethyl-6-(6-trifluoromethyl-pyridin-3-yl)-pyrimidin-2-yl]-pyridin-2-yl}-thiophene-2-sulfonic acid amide;
   3-{4-[4-Methyl-6-(6-trifluoromethyl-pyridin-3-yl)-pyrimidin-2-yl]-pyridin-2-yl}-benzenesulfonamide; and
   5-{4-[4-Methyl-6-(6-trifluoromethyl-pyridin-3-yl)-pyrimidin-2-yl]-pyridin-2-yl}-thiophene-2-sulfonic acid amide.

13. A compound of formula (Ic):

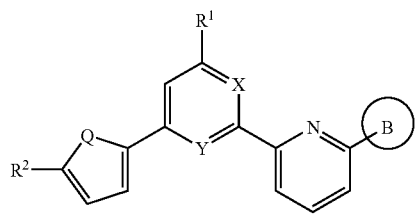

(Ic)

wherein
X and Y are N;
Q is S, O, —CH=N— or —N=CH—;
B is an optionally substituted aryl or an optionally substituted 5 or 6 membered heteroaryl, wherein the substituents are selected from the group consisting of:
   halo,
   nitro,
   $C_{1-6}$-alkyl optionally substituted by hydroxy,
   $NR^aR^b$, wherein $R^a$ and $R^b$ are independently H, $C_{1-6}$-alkyl or $-(CO)-C_{1-6}$-alkyl,
   $-S-C_{1-6}$-alkyl,
   $-(SO_2)-OH$,
   $-(SO_2)-C_{1-6}$-alkyl,
   $-(SO_2)-NR^cR^d$, wherein $R^c$ and $R^d$ are independently:
      H,
      $C_{1-6}$-alkyl optionally substituted by hydroxy,
      $C_{1-6}$-haloalkyl,
      $C_{1-6}$-alkoxy,
      $-(CO)C_{1-6}$-alkyl optionally substituted by $C_{1-6}$-alkoxy,
      $-(CH_2CH_2O)_nCHR^e$, wherein $R^e$ is H or $CH_2OH$ and n is 1, 2, 3, 4, 5, 6, 7, 8, 9 or 10,
      $-(CH_2)_m$-aryl, wherein m is 1 or 2 and the aryl is optionally substituted by halo or $C_{1-6}$-alkoxy,
      $-(CH_2)_p-C_{3-6}$-cycloalkyl, wherein p is 0 or 1, 5 or 6-membered heterocycloalkyl,
   $-(SO_2)-NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of:
      hydroxy, $C_{1-6}$-alkyl, $C_{1-6}$-alkoxy which is optionally substituted by
      hydroxy, and 5 or 6 membered heteroaryloxy,
   $NHSO_2-C_{1-6}$-alkyl, and
   $NHSO_2-NR^hR^i$ wherein $R^h$ and $R^i$ are independently H, $C_{1-6}$-alkyl, $-(CO)O-C_{1-6}$-alkyl, or $R^h$ and $R^i$ together with the nitrogen atom to which they are attached form a 4, 5 or 6 membered heterocycloalkyl ring optionally containing a further heteroatom selected from nitrogen, oxygen or sulphur, wherein said 4, 5 or 6 membered heterocycloalkyl ring is optionally substituted by $C_{1-6}$-alkyl,
$R^1$ is H, halogen, $C_{1-6}$-alkyl optionally substituted by hydroxy, $C_{1-6}$-alkoxy, $C_{1-6}$-haloalkyl, or $C_{3-6}$-cycloalkyl; and
$R^2$ is selected from the group consisting of cyano, halogen, $C_{1-6}$-haloalkyl, $C_{1-6}$-alkoxy, $C_{1-6}$-haloalkoxy, $C_{1-6}$-alkyl and $C_{3-6}$-cycloalkyl;
   or is $NR^jR^k$ wherein $R^j$ and $R^k$ are each independently selected from the group consisting of
      H, $C_{3-8}$-cycloalkyl, aryl, heteroaryl having from 5 to 12 ring atoms and $C_{1-6}$-alkyl which optionally substituted by one or more substituent(s) selected from the group consisting of halogen, hydroxy, $C_{3-8}$-cycloalkyl, aryl, heteroaryl having from 5 to 12 ring atoms and $-NR^lR^m$, wherein $R^l$ and $R^m$ are independently selected from the group consisting of H and $C_{1-6}$-alkyl;
      or $R^l$ and $R^m$ can, together with the nitrogen atom to which they are attached, form an optionally substituted heterocyclic group comprising 5 to 12 ring atoms optionally containing a further heteroatom selected from nitrogen, oxygen or sulphur, wherein said heterocyclic group is optionally substituted by one, two, three, four or five substituents are selected from the group consisting of halogen, hydroxy, $C_{1-6}$-alkyl and $C_{1-6}$-haloalkyl;
or a pharmaceutically acceptable salt thereof.

14. The compound of claim 13, wherein B is an optionally substituted aryl or an optionally substituted 5 or 6 membered heteroaryl, wherein the substituent is $NR^aR^b$, wherein $R^a$ and $R^b$ are H and $-(SO_2)-NR^cR^d$, wherein $R^c$ and $R^d$ are independently H, $C_{1-6}$-alkyl, or $-(CO)C_{1-6}$-alkyl.

15. The compound of claim 14, selected from the group consisting of:
   N-tert-Butyl-3-{6-[4-methyl-6-(6-trifluoromethyl-pyridin-3-yl)-pyrimidin-2-yl]-pyridin-2-yl}-benzenesulfonamide;
   N-tert-Butyl-3-{6-[4-methyl-6-(6-trifluoromethyl-pyridin-3-yl)-pyrimidin-2-yl]-pyridin-2-yl}-benzenesulfonamide;
   3-{6-[4-Methyl-6-(5-trifluoromethyl-pyridin-2-yl)-pyrimidin-2-yl]-pyridin-2-yl}-benzenesulfonamide; and
   3-{6-[4-Methyl-6-(6-trifluoromethyl-pyridin-3-yl)-pyrimidin-2-yl]-pyridin-2-yl}-benzenesulfonamide.

16. A compound of formula (Id):

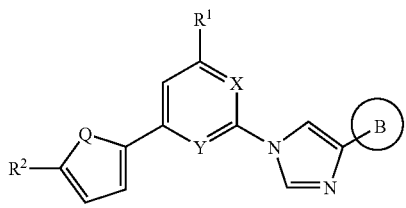

wherein
X and Y are N;
Q is S, O, —CH=N— or —N=CH—;
B is an optionally substituted aryl or an optionally substituted 5 or 6 membered heteroaryl, wherein the substituents are selected from the group consisting of:
halo,
nitro,
$C_{1-6}$-alkyl optionally substituted by hydroxy,
$NR^aR^b$, wherein $R^a$ and $R^b$ are independently H, $C_{1-6}$-alkyl or —(CO)—$C_{1-6}$-alkyl,
—S—$C_{1-6}$-alkyl,
—($SO_2$)—OH,
—($SO_2$)—$C_{1-6}$-alkyl,
—($SO_2$)—$NR^cR^d$, wherein $R^c$ and $R^d$ are independently:
H,
$C_{1-6}$-alkyl optionally substituted by hydroxy,
$C_{1-6}$-haloalkyl,
$C_{1-6}$-alkoxy,
—(CO)$C_{1-6}$-alkyl optionally substituted by $C_{1-6}$-alkoxy,
—($CH_2CH_2O$)$_n$$CHR^e$, wherein $R^e$ is H or $CH_2OH$ and n is 1, 2, 3, 4, 5, 6, 7, 8, 9 or 10,
—($CH_2$)$_m$-aryl, wherein m is 1 or 2 and the aryl is optionally substituted by halo or $C_{1-6}$-alkoxy,
—($CH_2$)$_p$—$C_{3-6}$-cycloalkyl, wherein p is 0 or 1, 5 or 6-membered heterocycloalkyl,
—($SO_2$)—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of:
hydroxy, $C_{1-6}$-alkoxy which is optionally substituted by
hydroxy, and 5 or 6 membered heteroaryloxy,
$NHSO_2$—$C_{1-6}$-alkyl, and
$NHSO_2$—$NR^hR^i$ wherein $R^h$ and $R^i$ are independently H, —(CO)O—$C_{1-6}$-alkyl, or $R^h$ and $R^i$ together with the nitrogen atom to which they are attached form a 4, 5 or 6 membered heterocycloalkyl ring optionally containing a further heteroatom selected from nitrogen, oxygen or sulphur, wherein said 4, 5 or 6 membered heterocycloalkyl ring is optionally substituted by $C_{1-6}$-alkyl,
$R^1$ is H, halogen, $C_{1-6}$-alkyl optionally substituted by hydroxy, $C_{1-6}$-alkoxy, $O_{1-6}$-haloalkyl, or $C_{3-6}$-cycloalkyl; and
$R^2$ is selected from the group consisting of cyano, halogen, $C_{1-6}$-haloalkyl, $C_{1-6}$-alkoxy, $C_{1-6}$-haloalkoxy, $C_{1-6}$-alkyl and $C_{3-6}$-cycloalkyl;

or is $NR^jR^k$ wherein $R^j$ and $R^k$ are each independently selected from the group consisting of
H, $C_{3-8}$-cycloalkyl, aryl, heteroaryl having from 5 to 12 ring atoms and $C_{1-6}$-alkyl which optionally substituted by one or more substituent(s) selected from the group consisting of halogen, hydroxy, $C_{3-8}$-cycloalkyl, aryl, heteroaryl having from 5 to 12 ring atoms and —$NR^lR^m$, wherein $R^l$ and $R^m$ are independently selected from the group consisting of H and $C_{1-6}$-alkyl;
or $R^l$ and $R^m$ can, together with the nitrogen atom to which they are attached, form an optionally substituted heterocyclic group comprising 5 to 12 ring atoms optionally containing a further heteroatom selected from nitrogen, oxygen or sulphur, wherein said heterocyclic group is optionally substituted by one, two, three, four or five substituents are selected from the group consisting of halogen, hydroxy, $C_{1-6}$-alkyl and $C_{1-6}$-haloalkyl;
or a pharmaceutically acceptable salt thereof.

17. The compound of claim 16, wherein B is an optionally substituted aryl or an optionally substituted 5 or 6 membered heteroaryl, wherein the substituent is $NR^aR^b$, wherein $R^a$ and $R^b$ are both H.

18. The compound of claim 17, selected from the group consisting of
5-{1-[4-Trifluoromethyl-6-(6-trifluoromethyl-pyridin-3-yl)-pyrimidin-2-yl]-1H-imidazol-4-yl}-pyridin-2-ylamine;
5-{1-[4-Difluoromethyl-6-(6-trifluoromethyl-pyridin-3-yl)-pyrimidin-2-yl]-1H-imidazol-4-yl}-pyridin-2-ylamine; and
5-{1-[4-Methyl-6-(6-trifluoromethyl-pyridin-3-yl)-pyrimidin-2-yl]-1H-imidazol-4-yl}-pyridin-2-ylamine.

19. The compound of claim 16, wherein B is an optionally substituted aryl or an optionally substituted 5 or 6 membered heteroaryl, wherein the substituent is $NR^aR^b$, wherein $R^a$ and $R^b$ are H and —($SO_2$)—$NR^cR^d$, wherein $R^c$ and $R^d$ are independently H, $C_{1-6}$-alkyl, or —(CO)$C_{1-6}$-alkyl.

20. The compound of claim 19, selected from the group consisting of
3-{1-[4-(5-Chloro-thiophen-2-yl)-6-trifluoromethyl-pyrimidin-2-yl]-1H-imidazol-4-yl}-benzenesulfonamide; and
5-{1-[4-Methyl-6-(6-trifluoromethyl-pyridin-3-yl)-pyrimidin-2-yl]-1H-imidazol-4-yl}-pyridin-2-ylamine.

21. A pharmaceutical composition comprising a compound of formula I

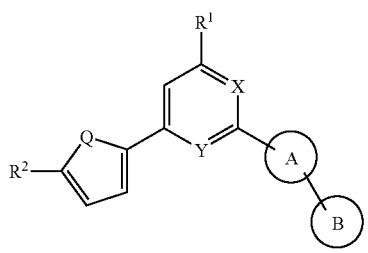

wherein
X and Y are N;
Q is S, O, —CH=N— or —N=CH—;
A is aryl or 5 or 6 membered heteroaryl each of which is optionally substituted by $C_{1-6}$-alkyl;

B is an optionally substituted 5 or 6 membered heteroaryl, wherein the substituents are selected from the group consisting of:
halo,
nitro,
$C_{1-6}$-alkyl optionally substituted by hydroxy,
$NR^aR^b$, wherein $R^a$ and $R^b$ are independently H, $C_{1-6}$-alkyl or —(CO)—$C_{1-6}$-alkyl,
—S—$C_{1-6}$-alkyl,
—($SO_2$)—OH,
—($SO_2$)—$C_{1-6}$-alkyl,
—($SO_2$)—$NR^cR^d$, wherein $R^c$ and $R^d$ are independently:
H,
$C_{1-6}$-alkyl optionally substituted by hydroxy,
$C_{1-6}$-haloalkyl,
$C_{1-6}$-alkoxy,
—(CO)$C_{1-6}$-alkyl optionally substituted by $C_{1-6}$-alkoxy,
—($CH_2CH_2O)_n CHR^e$, wherein $R^e$ is H or $CH_2OH$ and n is 1, 2, 3, 4, 5, 6, 7, 8, 9 or 10,
—($CH_2)_m$-aryl, wherein m is 1 or 2 and the aryl is optionally substituted by halo or $C_{1-6}$-alkoxy,
—($CH_2)_p$—$C_{3-6}$-cycloalkyl, wherein p is 0 or 1, 5 or 6-membered heterocycloalkyl,
—($SO_2$)—$NR^fR^g$, wherein $R^f$ and $R^g$ together with the nitrogen atom to which they are attached form a 4, 5 or 6 membered heterocycloalkyl ring optionally containing a further heteroatom selected from nitrogen, oxygen, sulphur and an $SO_2$ group, wherein said 4, 5 or 6 membered heterocycloalkyl ring is optionally substituted by a substituent selected from the group consisting of:
hydroxy, $C_{1-6}$-alkyl, $C_{1-6}$-alkoxy which is optionally substituted by
hydroxy, and 5 or 6 membered heteroaryloxy,
$NHSO_2$—$C_{1-6}$-alkyl, and
$NHSO_2$—$NR^hR^i$ wherein $R^h$ and $R^i$ are independently H, $C_{1-6}$-alkyl, —(CO)O—$C_{1-6}$-alkyl, or $R^h$ and $R^i$ together with the nitrogen atom to which they are attached form a 4, 5 or 6 membered heterocycloalkyl ring optionally containing a further heteroatom selected from nitrogen, oxygen or sulphur, wherein said 4, 5 or 6 membered heterocycloalkyl ring is optionally substituted by $C_{1-6}$-alkyl,
$R^1$ is H, halogen, $C_{1-6}$-alkyl optionally substituted by hydroxy, $C_{1-6}$-alkoxy, $C_{1-6}$-haloalkyl, or $C_{3-6}$-cycloalkyl; and
$R^2$ is selected from the group consisting of cyano, halogen, $C_{1-6}$-haloalkyl, $C_{1-6}$-alkoxy, $C_{1-6}$-haloalkoxy, $C_{1-6}$-alkyl and $C_{3-6}$-cycloalkyl;
or is $NR^jR^k$ wherein $R^j$ and $R^k$ are each independently selected from the group consisting of
H, $C_{3-8}$-cycloalkyl, aryl, heteroaryl having from 5 to 12 ring atoms and $C_{1-6}$-alkyl which optionally substituted by one or more substituent(s) selected from the group consisting of halogen, hydroxy, $C_{3-8}$-cycloalkyl, aryl, heteroaryl having from 5 to 12 ring atoms and —$NR^lR^m$, wherein $R^l$ and $R^m$ are independently selected from the group consisting of H and $C_{1-6}$-alkyl;
or $R^l$ and $R^m$ can, together with the nitrogen atom to which they are attached, form an optionally substituted heterocyclic group comprising 5 to 12 ring atoms optionally containing a further heteroatom selected from nitrogen, oxygen or sulphur, wherein said heterocyclic group is optionally substituted by one, two, three, four or five substituents are selected from the group consisting of halogen, hydroxy, $C_{1-6}$-alkyl and $C_{1-6}$-haloalkyl;
or a pharmaceutically acceptable salt thereof
and a pharmaceutically acceptable carrier.

22. A pharmaceutical composition comprising a therapeutically effective amount of a compound of claim 3 and a pharmaceutical acceptable carrier.

23. A pharmaceutical composition comprising a therapeutically effective amount of a compound of claim 8 and a pharmaceutical acceptable carrier.

24. A pharmaceutical composition comprising a therapeutically effective amount of a compound of claim 13 and a pharmaceutical acceptable carrier.

25. A pharmaceutical composition comprising a therapeutically effective amount of a compound of claim 16 and a pharmaceutical acceptable carrier.

* * * * *